(12) United States Patent
Bailly et al.

(10) Patent No.: US 9,724,562 B2
(45) Date of Patent: Aug. 8, 2017

(54) WEARABLE USB DEVICE ASSEMBLY

(71) Applicant: NIKE, Inc., Beaverton, OR (US)

(72) Inventors: Devin Bailly, Beaverton, OR (US);
Keith Folske, Wilsonville, OR (US);
Holli Pheil, Portland, OR (US);
Summer Schneider, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 14/723,901

(22) Filed: May 28, 2015

(65) Prior Publication Data
US 2016/0346609 A1    Dec. 1, 2016

(51) Int. Cl.
| | |
|---|---|
| *A63B 24/00* | (2006.01) |
| *G06F 13/38* | (2006.01) |
| *H04Q 9/00* | (2006.01) |
| *G06K 9/00* | (2006.01) |
| *A61B 5/103* | (2006.01) |
| *A61B 5/00* | (2006.01) |

(52) U.S. Cl.
CPC ........ *A63B 24/0062* (2013.01); *G06F 13/385* (2013.01); *G06K 9/00342* (2013.01); *H04Q 9/00* (2013.01); *A61B 5/1038* (2013.01); *A61B 5/6807* (2013.01); *H04Q 2209/30* (2013.01); *H04Q 2209/40* (2013.01); *H04Q 2209/86* (2013.01)

(58) Field of Classification Search
CPC . A63B 24/062; A63B 2220/836; A61B 5/024; A61B 5/1118; A61B 5/6831; A61B 5/6831

USPC .................................................. 340/539.12
See application file for complete search history.

(56) References Cited

U.S. PATENT DOCUMENTS

| | | | |
|---|---|---|---|
| 2012/0082013 A1 | 4/2012 | Yeung et al. | |
| 2013/0106684 A1* | 5/2013 | Weast | G06F 19/3481 345/156 |
| 2013/0274904 A1 | 10/2013 | Coza et al. | |
| 2014/0074266 A1 | 3/2014 | Tchao et al. | |
| 2015/0061891 A1 | 3/2015 | Oleson et al. | |
| 2015/0342529 A1* | 12/2015 | Gassoway | A61B 5/0082 600/301 |
| 2016/0066858 A1* | 3/2016 | Crawford | A61B 5/7264 600/301 |

FOREIGN PATENT DOCUMENTS

WO    2010104879 A2    9/2010

OTHER PUBLICATIONS

Aug. 23, 2016—(WO) ISR & WO—App. No. PCT/US16/032009.

* cited by examiner

*Primary Examiner* — Kevin Kim
(74) *Attorney, Agent, or Firm* — Banner & Witcoff, Ltd.

(57) ABSTRACT

Tracking and monitoring athletic activity offers individuals with additional motivation to continue such behavior. An individual may track his or her athletic activity by utilizing a wearable device assembly configured to monitor various aspects of athletic performance. In some embodiments, the wearable device assembly may comprise a USB-type device having athletic functionality and configured to transmit to and/or receive data from an external computing device.

19 Claims, 24 Drawing Sheets

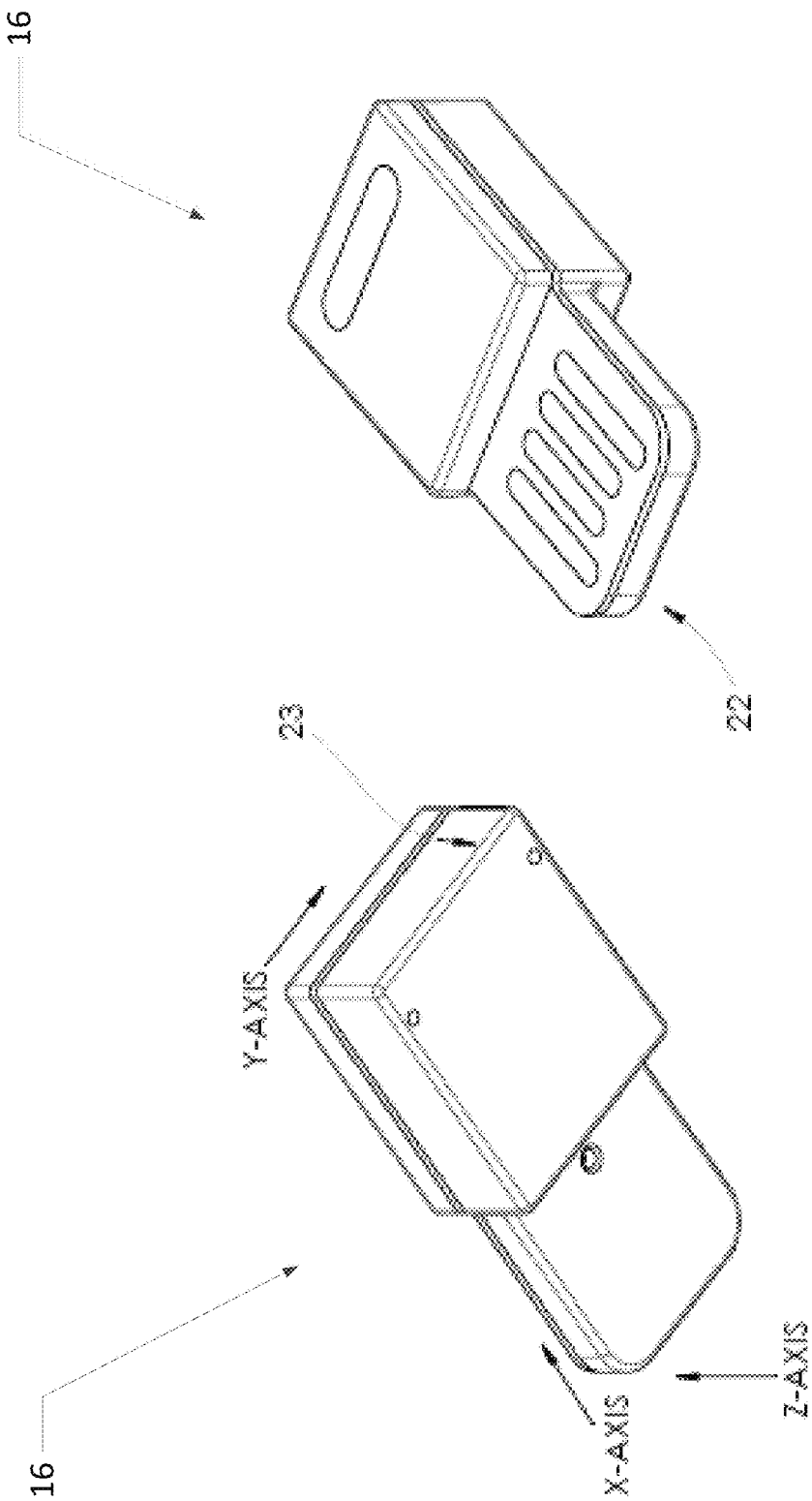

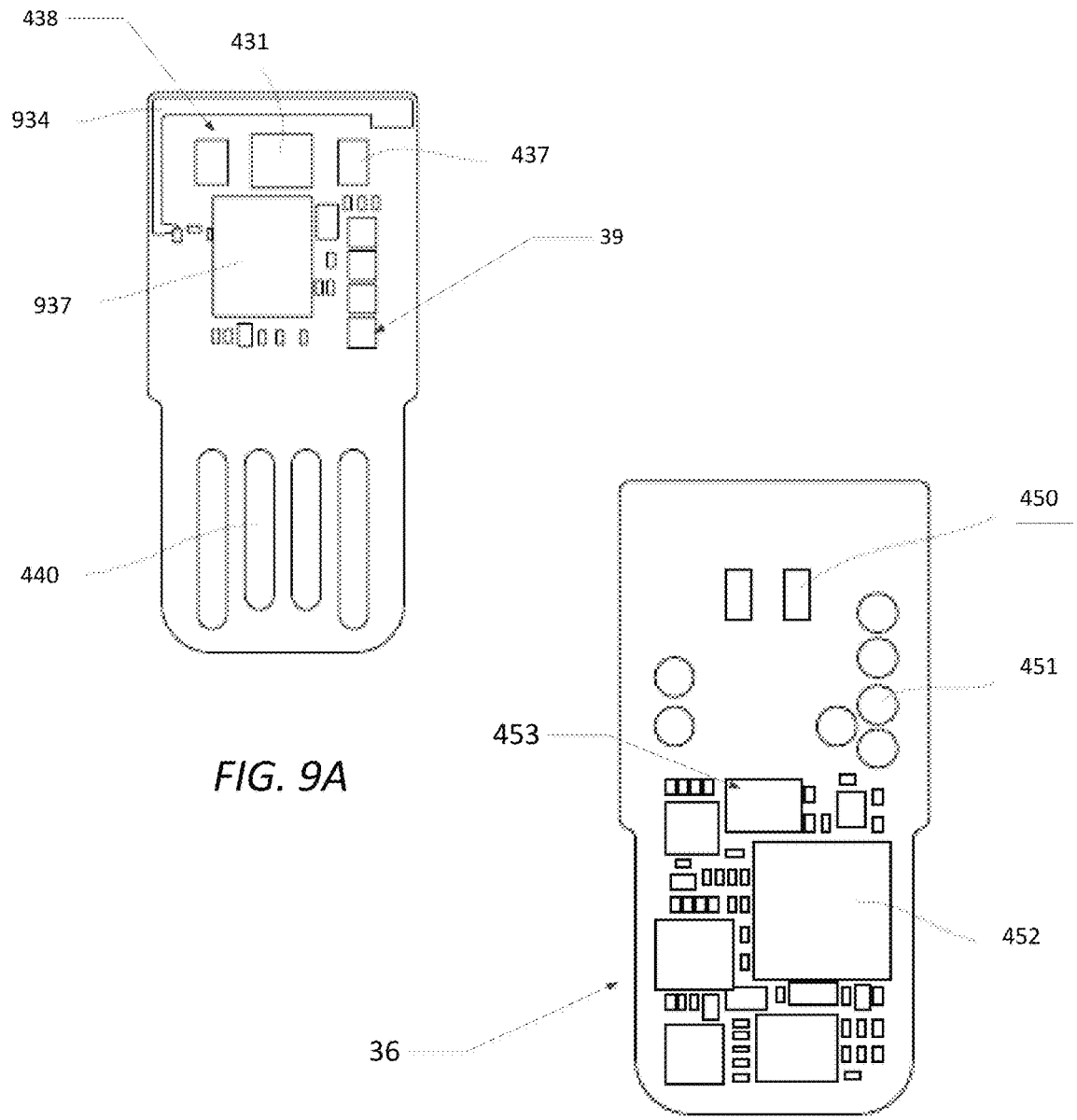

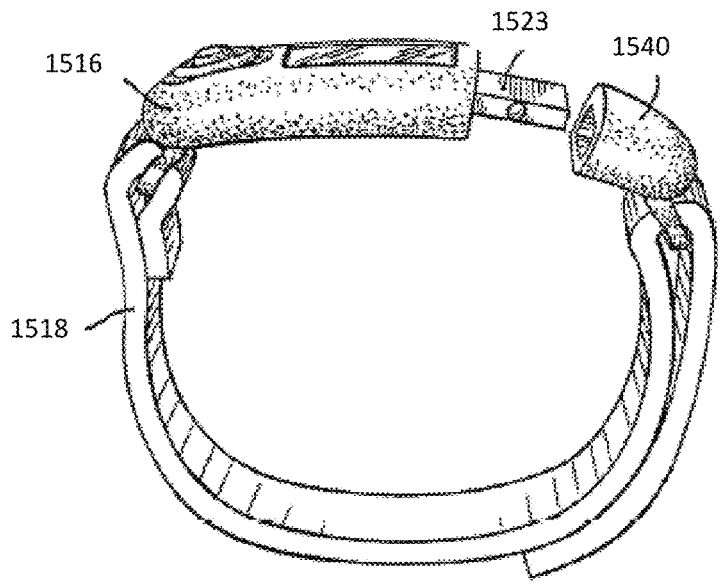
FIG. 15A
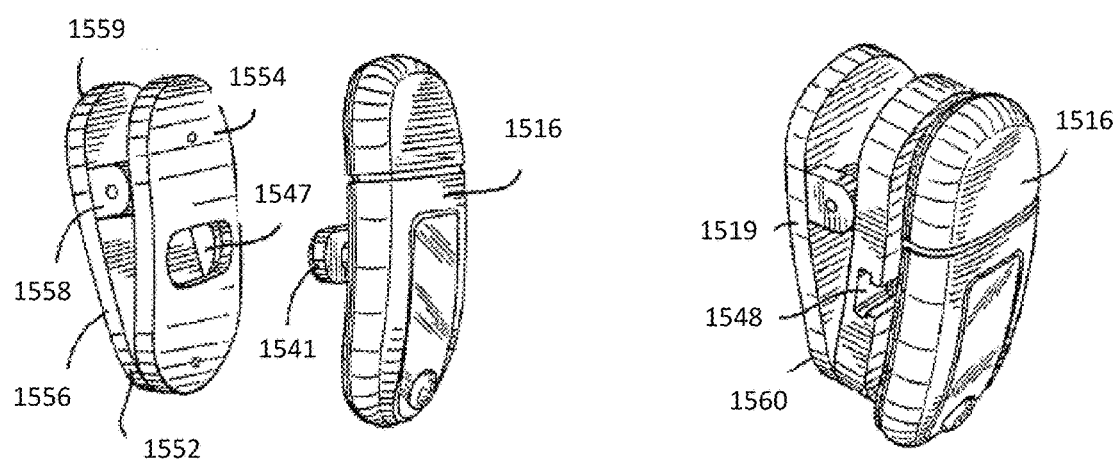
FIG. 15B
FIG. 15C

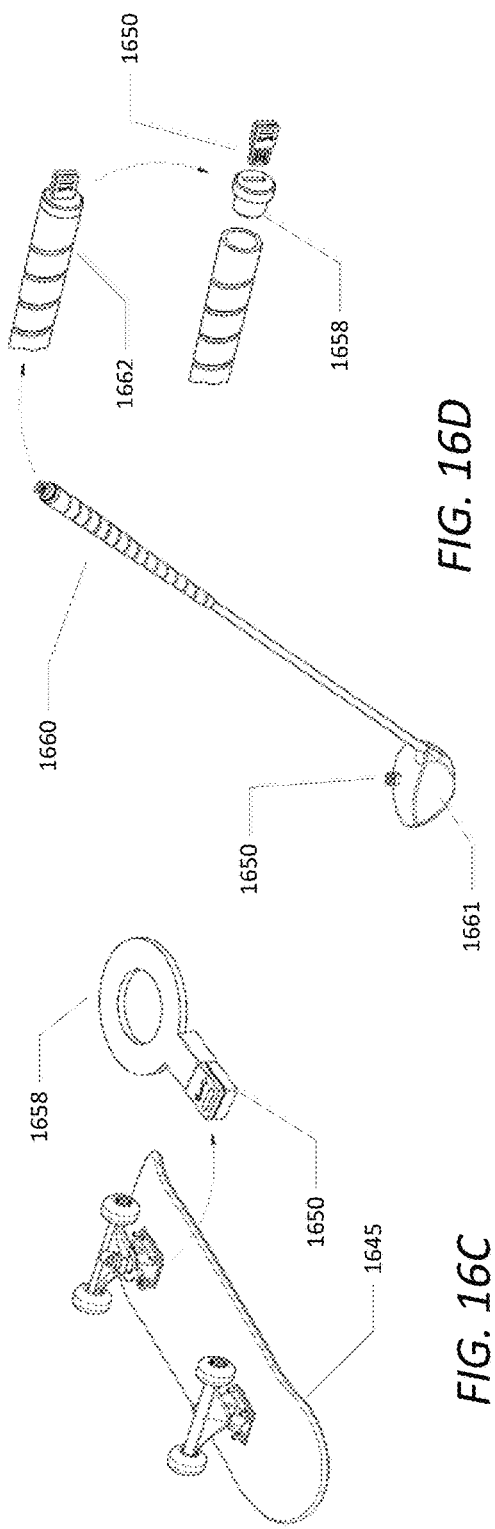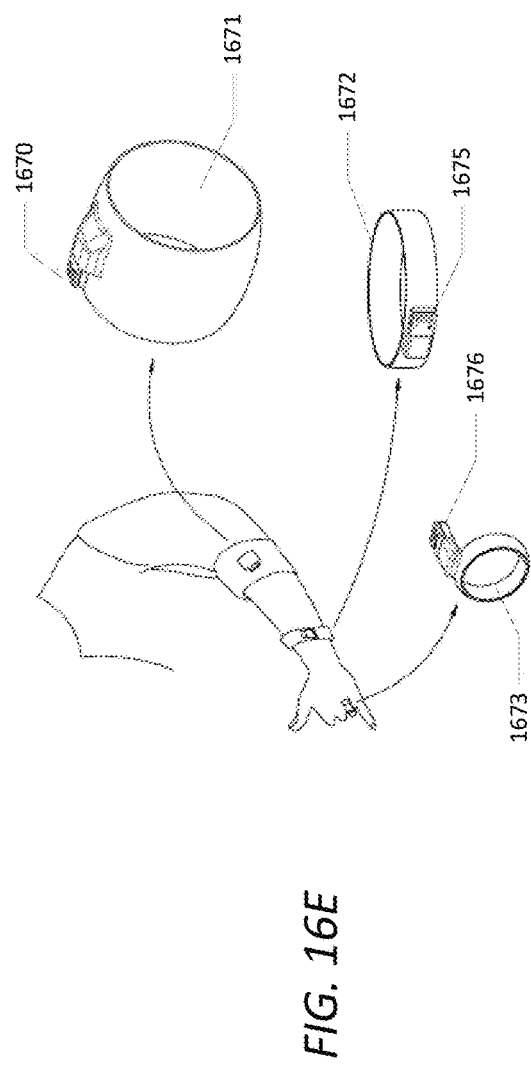
FIG. 16C
FIG. 16D
FIG. 16E

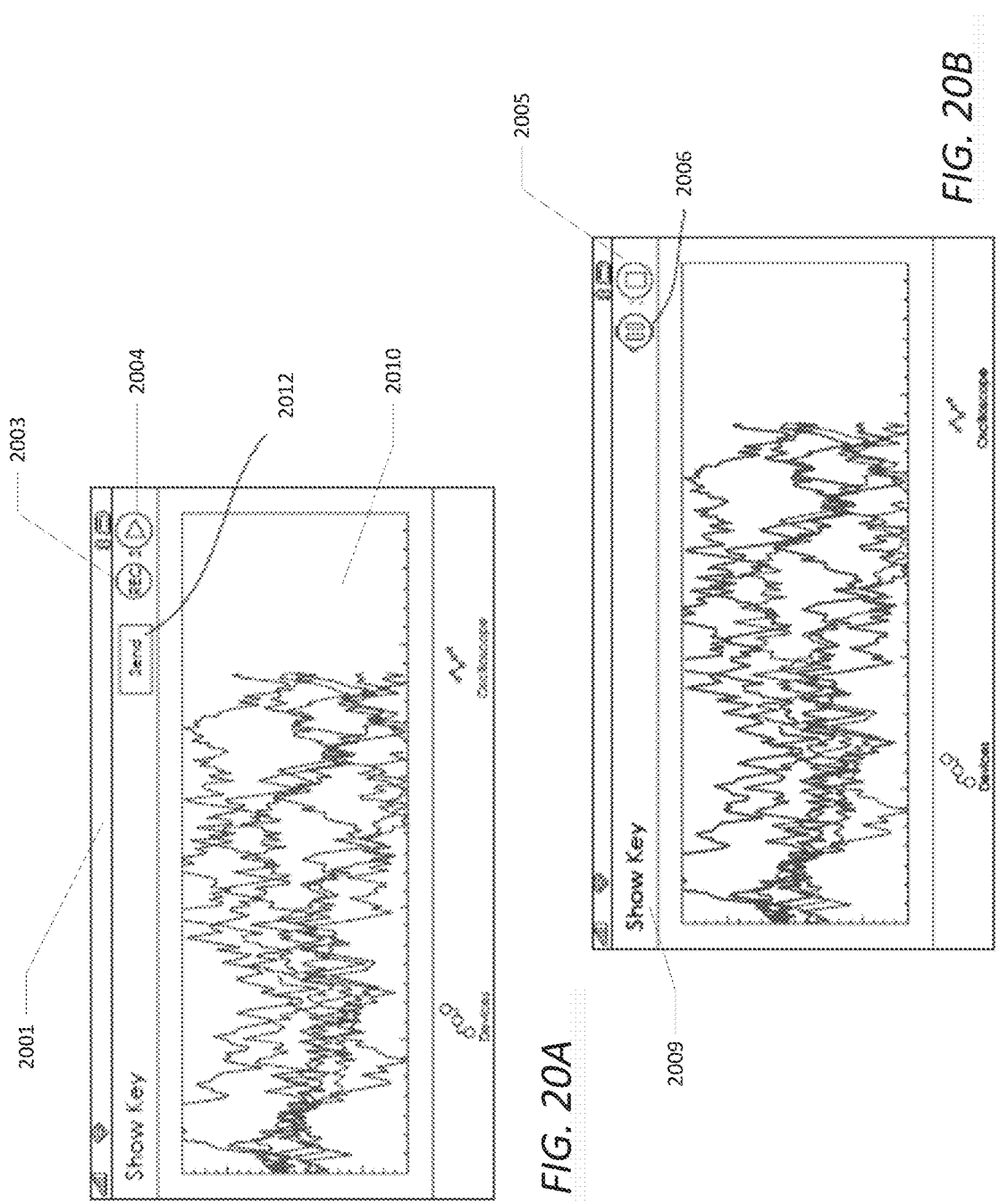

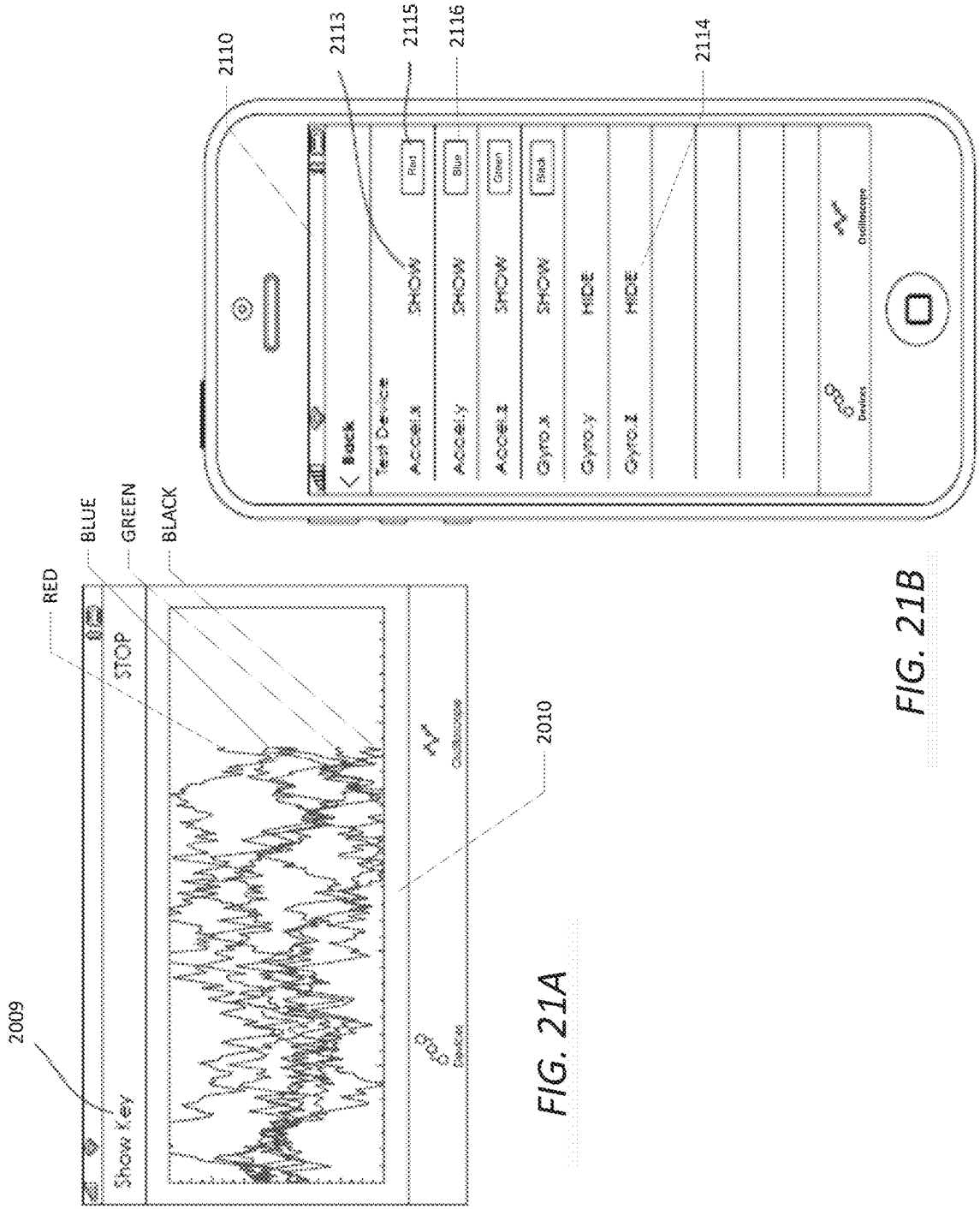

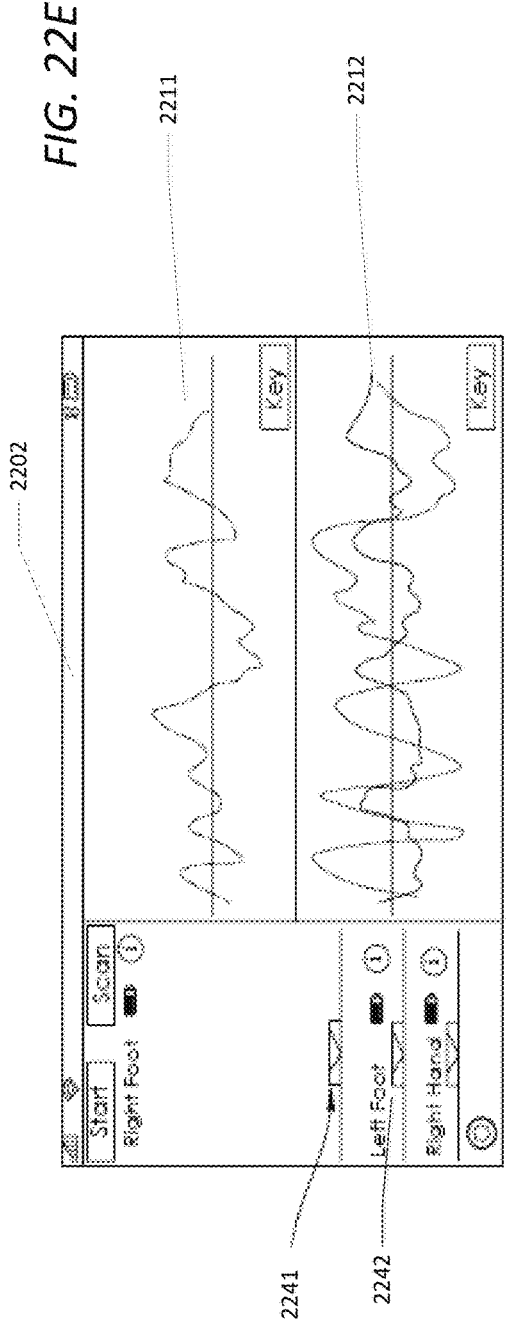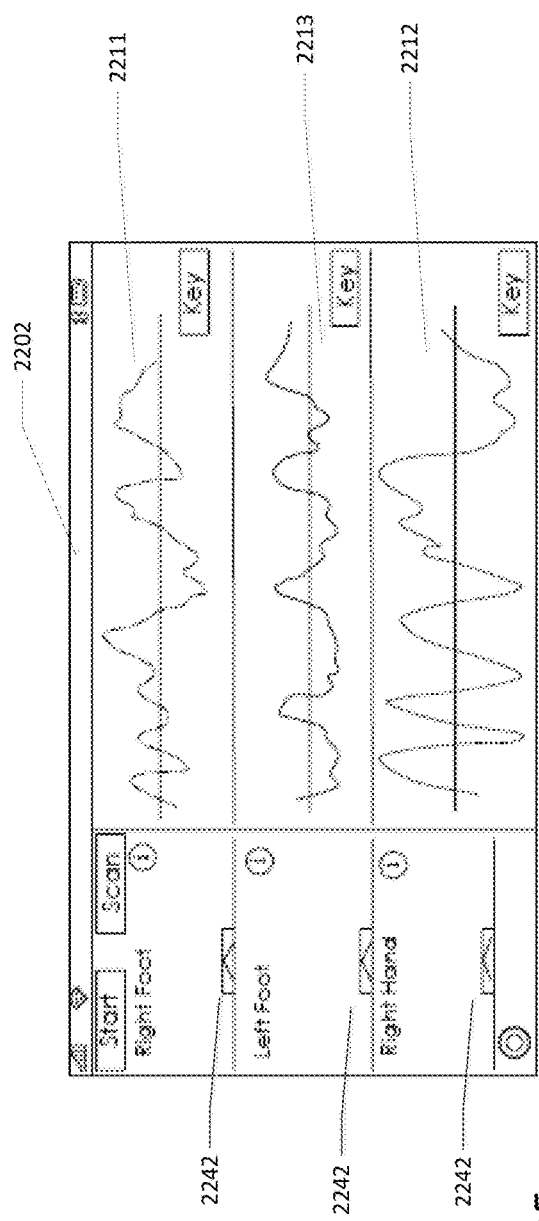
FIG. 22E
FIG. 22F

WEARABLE USB DEVICE ASSEMBLY

TECHNICAL FIELD

Aspects of the present disclosure relates generally to a USB type device, and more particularly, to a wearable USB type device having athletic functionality.

BACKGROUND OF THE INVENTION

Exercise and fitness have become increasingly popular and the benefits from such activities are well known. Various types of technology have been incorporated into the fitness industry and other athletic activities. For example, a wide variety of portable electronic devices are available for use in fitness activity such as MP3 or other audio players, radios, portable televisions, DVD players, or other audio/video playing devices, watches, GPS systems, pedometers, mobile telephones, pagers, beepers, and the like. Many fitness enthusiasts or athletes use one or more of these devices when exercising or training to keep them entertained, to provide and/or compare athletic performance data, or to keep them in contact with others etc.

Advances in technology have also provided more sophisticated athletic performance monitoring systems. Athletic performance monitoring systems enable easy and convenient monitoring of many physical and/or physiological characteristics associated with exercise and fitness activity, or other athletic performances including, for example, speed and distance data, altitude data, GPS data, heart rate, pulse rate, blood pressure data, body temperature, and the like. This data can be provided to a user through a portable electronic device carried by the user.

For example, athletes often wear portable athletic monitoring devices to keep track of time, distance, pace, laps, and other various performance metric etc. Such devices, however, are oftentimes not user friendly and cumbersome to use. Consequently, the wearer may not utilize the device to its full potential, or may need to wear a second monitoring device to obtain different athletic performance monitoring abilities not provided by the first monitoring device. Accordingly, while certain monitoring devices having athletic functionality provide a number of advantageous features, they nevertheless have certain limitations. For example, some athletic performance monitoring systems may have limited ability to further upload data to a personal computer or other location for further review and consideration, or such data transfer is cumbersome for the user. As another example, some athletic performance monitoring systems may require the user to remove the wearable device and/or stop a current athletic activity when the monitoring devices is low on power and/or requires a power charge. Aspects of the present disclosure seek to overcome certain of these limitations and other drawbacks of the prior art, and to provide new features not heretofore available.

A full discussion of the features and advantages of the present disclosure is deferred to the following detailed description, which proceeds with reference to the accompanying drawings.

SUMMARY OF THE INVENTION

The following presents a general summary of aspects of the present disclosure in order to provide a basic understanding of at least some of its aspects. This summary is not an extensive overview of the present disclosure. It is not intended to identify key or critical elements of the present disclosure or to delineate the scope of the present disclosure. The following summary merely presents some concepts of the present disclosure in a general form as a prelude to the more detailed description provided below.

Aspects of the present disclosure provide a USB-type device having athletic functionality. According to one aspect of the present disclosure, an electronic module may be configured to measure the athletic performance of a user. The electronic module may include a communication connector, such that the electronic module may be configured to be plugged into a computer of the user. In an exemplary embodiment, the communication connector may be in the form of a USB (Universal Serial Bus) connector. When the communication connector is inserted into the computer, athletic performance data recorded by the electronic module can be uploaded to the computer as well as a remote site accessed by the computer. The remote site may be a site dedicated to the tracking, analyzing and display of athletic performance. In a further exemplary embodiment, data from the remote site and the user's computer can be transferred to the electronic module for enhanced operability for the user.

According to a further aspect of the present disclosure, the USB connector may be fixedly attached to the housing of the electronic module, resulting in a USB-type device. The USB device may be used as part of a device assembly wherein the USB device is attached to a receiver member and/or a carrier. In some embodiments, the USB device may include one or more additional components, such that the USB device is wearable by the user. In addition, and as will be described in more detail below, the USB device may include a controller (or other suitable device unit) that communicates with a sensor to record and monitor athletic performance as an overall athletic performance monitoring system.

According to another aspect of the present disclosure, the USB device may be connected to a receiver member (e.g., a cap, closure member, etc.). The receiver member may include an internal space for accommodating at least a portion of the USB device (e.g., a female USB connector), such that the receiver member may be removably engaged with the USB device. In one exemplary embodiment, the USB device has a projection member and the receiver member has an aperture. The projection member (or protrusion) is inserted into the aperture wherein the USB device is connected to the receiver member. It is understood that the protrusion/aperture structures could be reversed on the components. In other aspects of the present disclosure, the receiver member may provide the USB device with additional functionality and/or monitoring abilities. In one exemplary embodiment, the receiver member may provide an additional power source for the USB device. In another exemplary embodiment, the receiver member may provide the USB device with additional monitoring capabilities and/or device functionality, such as geolocation features, altitude monitoring, temperature monitoring, NFC communications, WI-FI communication, Bluetooth communications, and the like.

According to a further aspect of the present disclosure, the receiver member may comprise a second USB device. In such arrangements, the second USB device may include a first end and a second end, wherein the first end includes a communication connector (e.g., a USB connector), and the second end includes an aperture configured to receive a USB connector of a USB device. Additionally or alternatively, the USB device may be connected to and/or operatively engaged with a receiver member having both a male USB connector and a female USB connector. In some embodiments, the receiver member may comprise a second USB device as described herein, the second USB device including a male USB connector and a female USB connector.

As discussed above, the USB device may include a housing supporting the USB device, a controller, and/or any other suitable device and/or hardware units therein. The housing has a structural configuration wherein the housing is water-resistant as well as impact resistant. In other aspects of the present disclosure, the housing may also support a battery or some other suitable power source. In still other aspects of the present disclosure, the housing may contain other suitable hardware structures, such as a memory unit or some other form of data storage, one or more lighting elements (e.g., LEDs, etc.), that may be utilized by the USB device and/or receiver member. As noted above, the USB device can be plugged into a computer wherein performance data can be automatically uploaded to a remote site for display and review.

According to a further aspect of the present disclosure, the carrier can take other forms wherein the USB device can be worn by a user in various different locations to obtain different physical and/or physiological characteristics of the wearer. Other features and advantages of the present disclosure will be apparent from the following specification taken in conjunction with the following drawings.

BRIEF DESCRIPTION OF THE DRAWINGS

To understand the present disclosure, it will now be described by way of example, with reference to the accompanying drawings in which:

FIGS. 7A-D are perspective views of USB-type device according to one or more aspects of the present disclosure;

FIGS. 9A-B are example cross-sectional views of a USB-type device as shown in FIG. 7B;

FIGS. 15A-C are perspective views of a wearable device assembly according to one or more aspects of the present disclosure;

FIGS. 16C-D are perspective views of a USB-type device engaged with athletic equipment according to one or more aspects of the present disclosure;

FIG. 16E are perspective views of a wearable device assembly according to one or more aspects of the present disclosure;

FIGS. 20A-B illustrate example user interface screens in accordance with one or more aspects of the disclosure;

FIGS. 21A-B illustrate example user interface screens in accordance with one or more aspects of the disclosure;

FIGS. 22A-F illustrate example user interface screens in accordance with one or more aspects of the disclosure;

DETAILED DESCRIPTION

Figure 1:
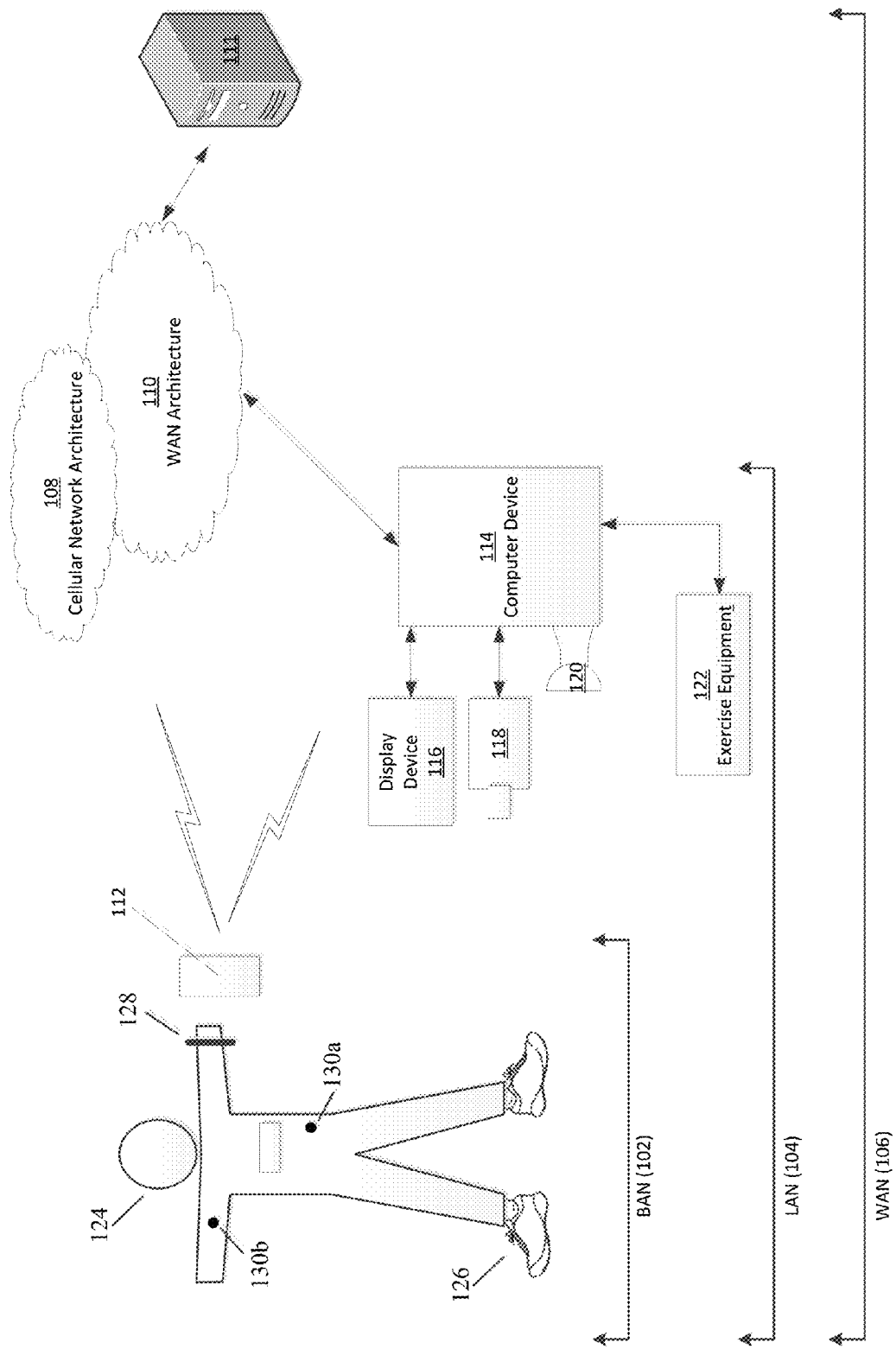
FIG. 1 illustrates an example system that may be configured to provide personal training and/or obtain data from the physical movements of a user in accordance with example embodiments.

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

Additionally, in the following description of various example embodiments of the present disclosure reference is made to the accompanying drawings, which form a part hereof, and in which are shown by way of illustration various example devices, systems, and environments in which aspects of the present disclosure may be practiced. It is to be understood that other specific arrangements of parts, example devices, systems, and environments may be utilized and structural and functional modifications may be made without departing from the scope of the present disclosure. Also, while the terms "top," "bottom," "front," "back," "side," and the like may be used in this specification to describe various example features and elements of the present disclosure, these terms are used herein as a matter of convenience, e.g., based on the example orientations shown in the figures. Nothing in this specification should be construed as requiring a specific three dimensional orientation of structures in order to fall within the scope of this disclosure.

The terms "performance" or "athletic performance," as used herein, mean any type of physical exertion or activity. Such activities include, but are not necessarily limited to: workout routines; training exercises; time trials; formal competitions; informal workouts; etc. "Performances" also include activities by persons not involved in physical exertion or activities for purposes of sport, such as children while playing, first responders, elderly or other assisted living and/or hospital patients, physical rehabilitation patients, and the like. The terms "athletic event" or "event" may be used synonymously with "athletic performance" or "performance" in this specification.

"Physical data" or "physical parameters" relating to a "performance" corresponds to any data associated with or relating to any measurable characteristic relating to the performance. Such physical data or parameters include, but are not limited to: physiological data or parameters (described in more detail below); elapsed time; time of day; distance covered; number of steps taken; speed; acceleration; angular velocity; angular acceleration; altitude; barometric pressure; gyroscope generated data; heading or directional data; ambient temperature data; ambient humidity data; wind direction data; wind speed data; global positioning satellite ("GPS") based data; etc.

Physiological data" or "physiological parameters" relating to a "performance" corresponds to any data associated with or relating to any measurable characteristic relating to a user's person or body. Such physiological data or parameters include, but are not limited to: heart rate; pulse rate; calories burned; calorie burn rate; METs; body weight; body temperature; blood pressure; electrocardiogram data; EEG data; etc.

I. Example Personal Training System
  A. Illustrative Networks

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
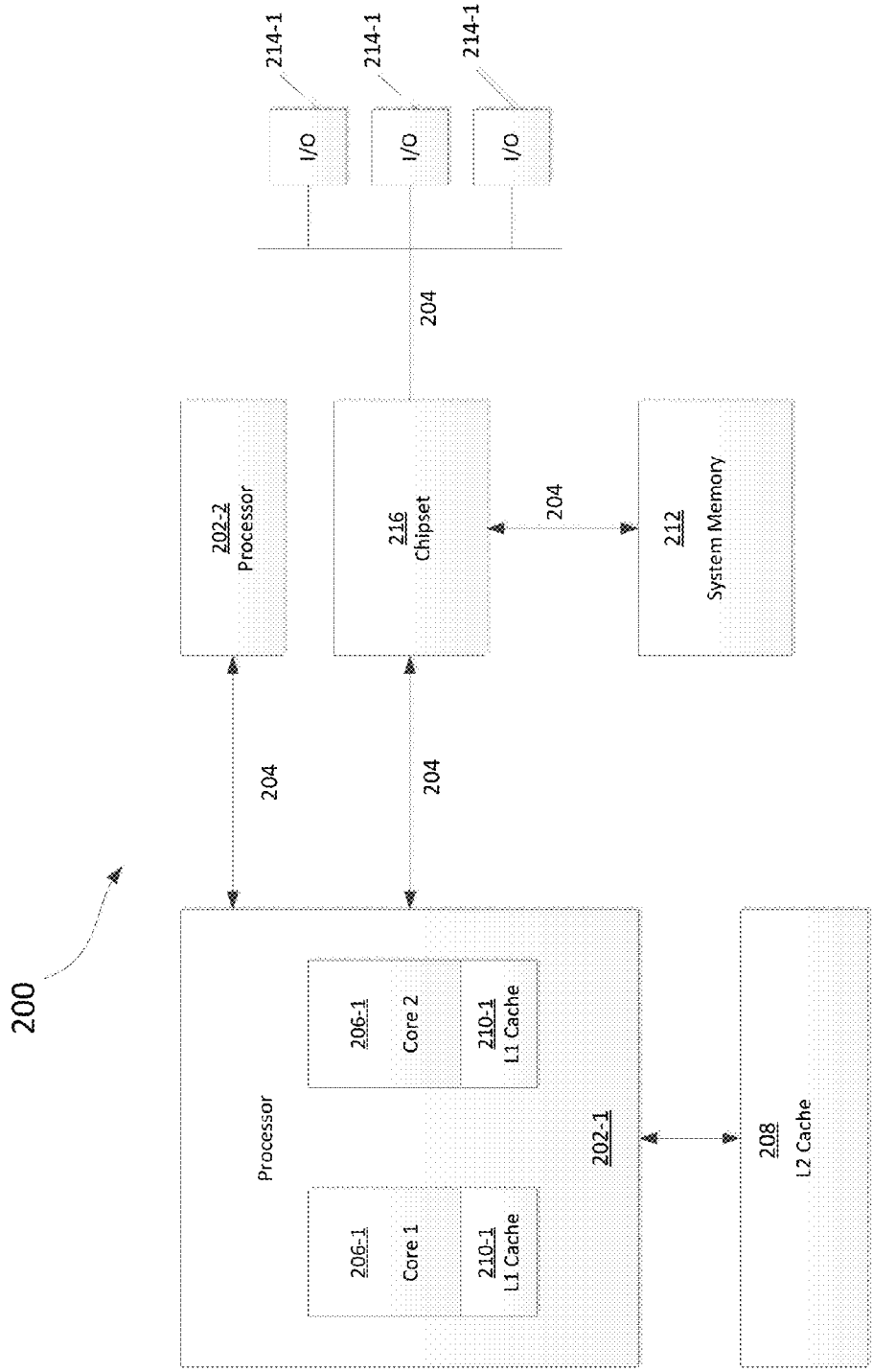
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
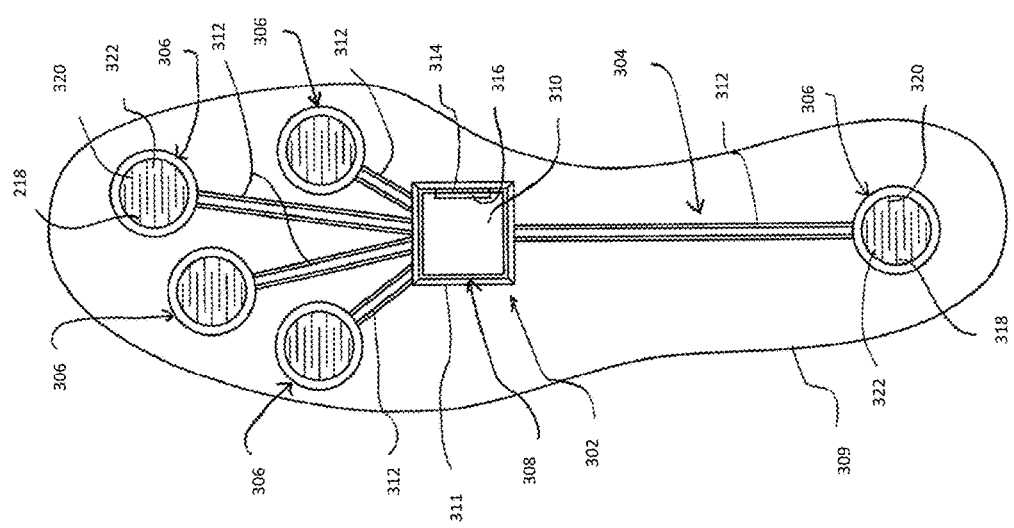
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318 and 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318 and 320. In some circumstances, this type of force-sensitive resistive behavior may be described as "contact-based resistance."

ii. Wrist-Worn Device

Figure 4:
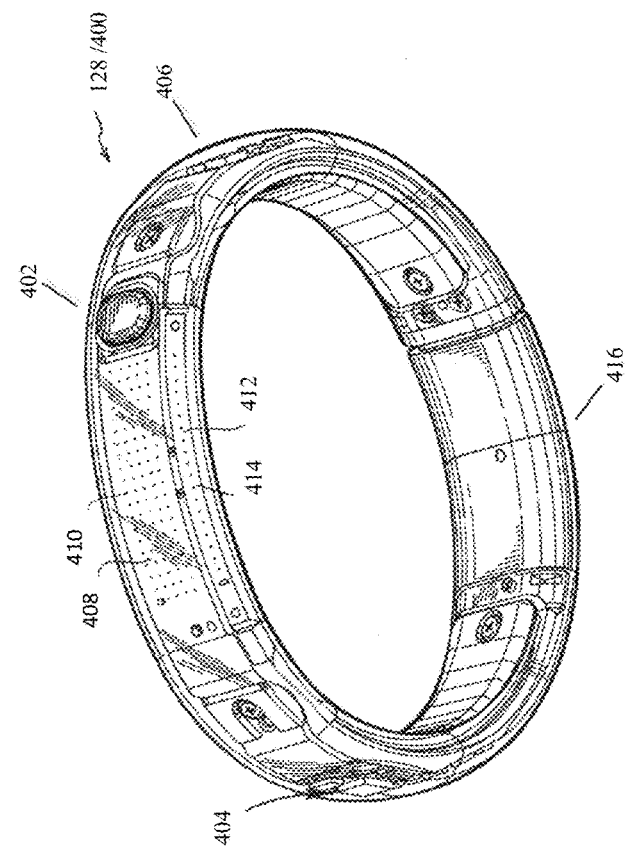
FIG. 4 shows another example sensor assembly that may be worn by a user in accordance with example embodiments.

As shown in the example embodiment depicted in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system 412 may provide a visual indication of goals, such as by illuminating a portion of lighting members of indicator system 412 to represent accomplishment towards one or more goals. In other aspects of the present disclosure, indicator system 412 may provide a visual notification that a communication connection is being attempted and/or has been established with another device, such as by illuminating one or more lighting members of indicator system 412 to represent that a communication connection is being attempted and/or has been established. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
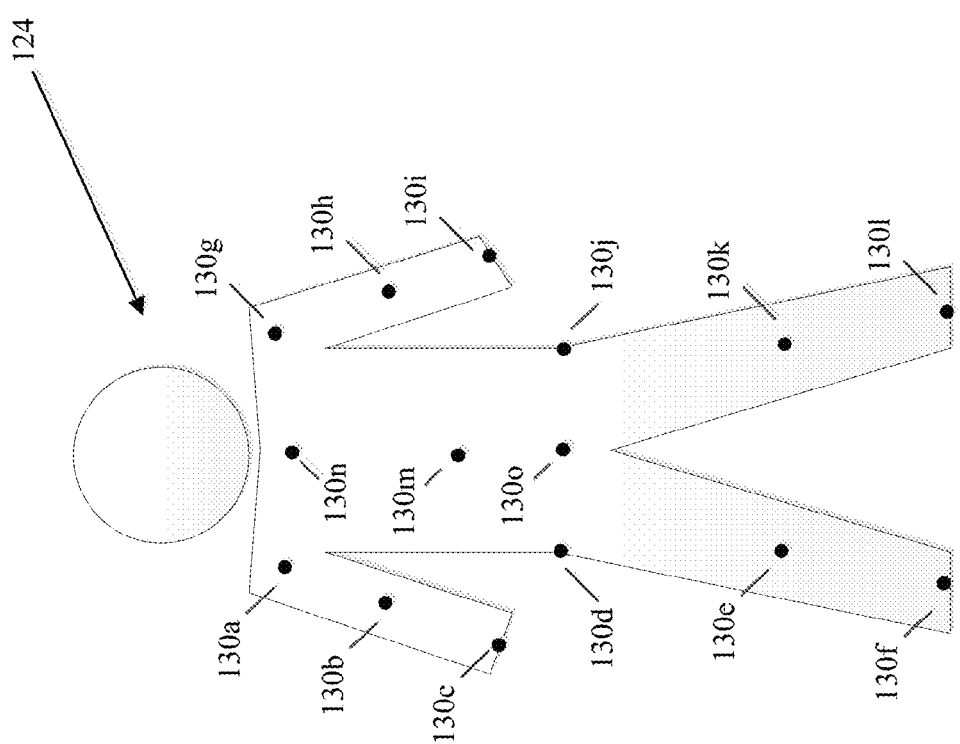
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130*m*-130*o*, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130*m*-130*o* may serve as a point for a center of moment location of user 124. In another embodiment, one or more locations may serve as a center of moment of specific body parts or regions.

II. General Description of Aspects of the Invention

The present disclosure provides a USB device having athletic functionality. According to one aspect of the present disclosure, the USB device may include a first electronic module may be configured to measure the athletic performance of a user. The first electronic module may include a communication connector, such that the first electronic module may be configured to be plugged into a computer of the user, as shown in FIG. 9. For example, the communication connector may be in the form of a USB (Universal Serial Bus) connector, thus resulting in a USB device.

In some embodiments, the USB device may be connected to a receiver member (e.g., a cap, closure member, etc.) having cooperative structure to removably connect the USB device with the receiver member. In one exemplary embodiment, the USB device has a protrusion (or projection member) and the receiver member has an opening or aperture, such as a female USB connector. The protrusion is inserted into the opening wherein the USB device is connected to the receiver member. In some embodiments, the receiver member may comprise a second USB device. In this arrangement, the second USB device may have at a first end a cooperative structure to removably engage a USB connector, and at a second end a communication connector (e.g., a USB connector). The USB connector of the first USB device may be configured to be engaged with and/or operatively connected to the first end of the second USB device.

The USB device may include a housing supporting an electronic module and/or other hardware/structural units therein. The housing has a structural configuration wherein the housing is water-resistant as well as impact resistant. In other aspects of the present disclosure, the housing may also support a battery or some other suitable power source. In still other aspects of the present disclosure, the housing may contain other suitable hardware structures, such as a memory unit or some other form of data storage, a communication unit (e.g., Bluetooth antenna), one or more lighting elements (e.g., LEDs, etc.), which may be utilized by the USB device and/or receiver member during a performance monitoring session.

In other aspects of the present disclosure, a controller of the USB device may communicate with a computing device executing software configured to control the USB device and/or to record and display performance data collected by the USB device and/or an operatively connected electronic component (e.g., a sensor, another USB device, etc.). In some embodiments, the software application may provide a user interface having certain features to modify and/or enhance the functionality of the USB device (or other electronic components). Additionally, the USB device can be plugged into a computer (see FIG. 9) wherein performance data and other information can be automatically uploaded to the computing device and/or a remote site for further display and review.

In other aspects of the present disclosure, the receiver member may provide the USB device with additional functionality and/or monitoring abilities. In one exemplary embodiment, the receiver member (e.g., closure member) may provide an additional power source for the USB device. In another exemplary embodiment, the receiver member may include therein an electronic module/component configured to provide the USB device with additional monitoring capabilities and/or device functionality, such as a global positioning system (GPS), geospace seismic recorder system (GSR), altitude monitoring, temperature monitoring, NFC communications, WI-FI communications, Bluetooth communications, and the like. For example, the USB device may include a GPS ("Global Positioning System") receiver and associated antenna for providing various GPS features to the USB device. Additionally or alternatively, the USB device may be engaged with a receiver member that includes a sensor (e.g., a GPS sensor or other suitable electronic component) that provides additional operational functionality to the USB device.

Aspects of the present disclosure further relate to other systems and/or devices that include receptacles or apertures for receiving USB connectors directly and/or operatively connected to electronic devices (or modules, components, etc.) for sensing one or more characteristics of performances of the various types described above. Performance sensing systems in accordance with this aspect of the present disclosure may include one or more of the following: (a) a housing defining a USB connector receiving chamber, wherein the USB connector receiving chamber is asymmetrical in at least one respect (e.g., sized and/or shaped so that the USB connector of a USB device will fit therein in a single or limited number of orientations); (b) a USB connector of a USB device received in the chamber, wherein the USB device provides data relating to at least one physical and/or physiological parameter associated with a performance, optionally wherein the USB device is structured such that it will fit into the housing in a single or limited number of orientations with respect to the housing; (c) a system for securing the USB device in and/or releasing the device e from the chamber; (d) a system for securing the housing to another object (e.g., an article of footwear or apparel, a piece of athletic equipment, and the like); (e) a power source for providing power to the USB device; (f) a data transmission system for transmitting data relating to the physical and/or physiological parameters from the USB device; (g) a data processing system for receiving the data from the data transmission system; (h) a display system for displaying data or information relating to the performance; (i) an activation and/or authentication system; etc.

A wide variety of potential structures and arrangements of these elements may be provided without departing from the present disclosure. For example, the data transmission system may be engaged with the USB device, or engaged with the housing and operatively coupled with the USB device. Additionally, at least some portion of the data processing system and/or data processing capabilities of the system may be included as part of the USB device, included as part of the housing (or electronic components therein), remote from the housing and connected via the data transmission system (including a wired or wireless connection, etc.), etc. If desired, at least some portions of the system, including the data processing system and/or display system, may be sized, shaped, and/or weighted so as to be carried by a user of the USB device and performance sensing system, e.g., during an athletic or other performance being sensed, e.g., as a wrist mounted system, as a belt or clothing mounted system, as a shoe mounted system, etc.

Any desired system for securing the USB device to and/or releasing the USB device from a housing may be used without departing from the present disclosure, including the various systems described above. Also, any desired system and/or structures for securing the housing to another object (including a person or a person's clothing) may be used without departing from the present disclosure, including, for example, a belt member, a band member, a shoe lace member, a clip or clasp member, an adhesive, a suction member, a fastener arrangement, and the like.

Still additional features of this aspect of the present disclosure relate to methods for providing performance sensing systems and/or methods for using performance sensing systems of the various types described above. In some aspects of the present disclosure, a performance monitoring system (or platform) may comprise one or more USB devices operatively connected to and/or in communication with a plurality of other electronic devices (e.g., USB devices, digital sensors, computing devices, and the like). Utilizing various USB devices, digital sensors, and other electronic devices (and/or components), the performance monitoring system may allow a user (or third-party) to collect meaningful sensor and performance data. Several USB and other electronic devices may collected performance data at the same time, with their respective sensor information time synchronized, such that the devices can be placed in various different locations (on a user, or in equipment, or in apparel, etc.) to collect different types of performance data.

II. Illustrative Examples of the Invention

While aspects of the present disclosure generally have been described above, the following detailed description, in conjunction with the Figures, provides even more detailed examples of athletic performance monitoring systems and methods in accordance with examples of the present disclosure. Those skilled in the art should understand, of course, that the following description constitutes descriptions of examples of the present disclosure and should not be construed as limiting the present disclosure in any way.

Figure 6:
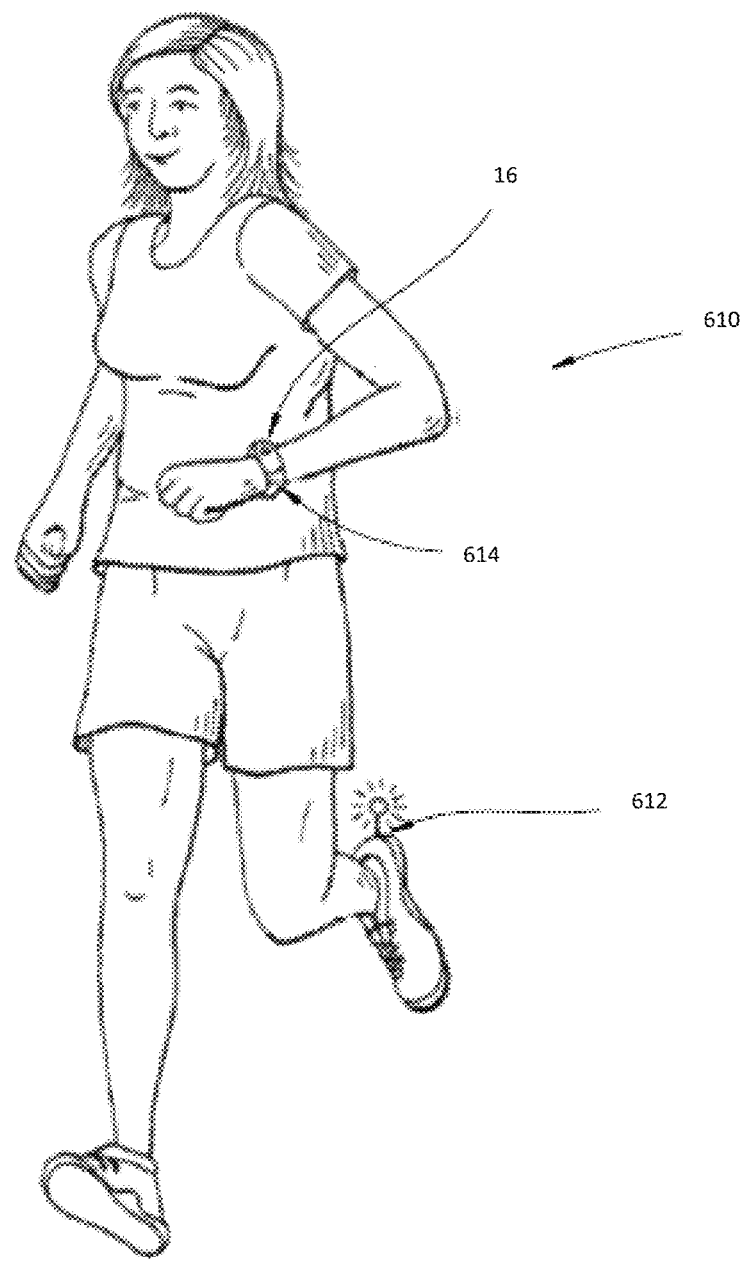
FIG. 6 is a perspective view of a runner wearing a device assembly of the present disclosure used in an athletic performance monitoring system.

FIG. 6 generally discloses an example athletic performance monitoring system 10 that in one exemplary embodiment of the present disclosure includes a wearable device having athletic functionality. Performance monitoring system 610 may include one or more of the features and/or functionality of example system 100 described above with respect to FIG. 1. As shown in the example embodiments depicted in FIG. 6, the athletic performance monitoring system 610 generally may include a sensor 612 and a wearable device assembly 614. In some aspects of the present disclosure, sensor 612 may be included within wearable device assembly 614. As discussed in greater detail below, the sensor 612 and wearable device assembly 614 wirelessly communicate with one another to record and monitor athletic performance. The wearable device assembly 614 generally includes a wearable device 16 that in one exemplary embodiment is a USB (Universal Serial Bus) type device 16, and a carrier (not shown) that in one exemplary embodiment takes the form of a wristband. Although reference to USB devices and/or protocols are made throughout this disclosure, those of ordinary skill in the art will appreciate that other data transfer protocols, which may or may not be serial in nature, may be utilized without departing from the scope of this disclosure. Further, other form factors, including mini-USB, micro-USB, and non-USB form factors may be utilized without departing from the scope of this disclosure. In one embodiment, any interface that is able to receive power and bi-directional data transfer is within the scope of this disclosure.

Figures 7C, 7D:
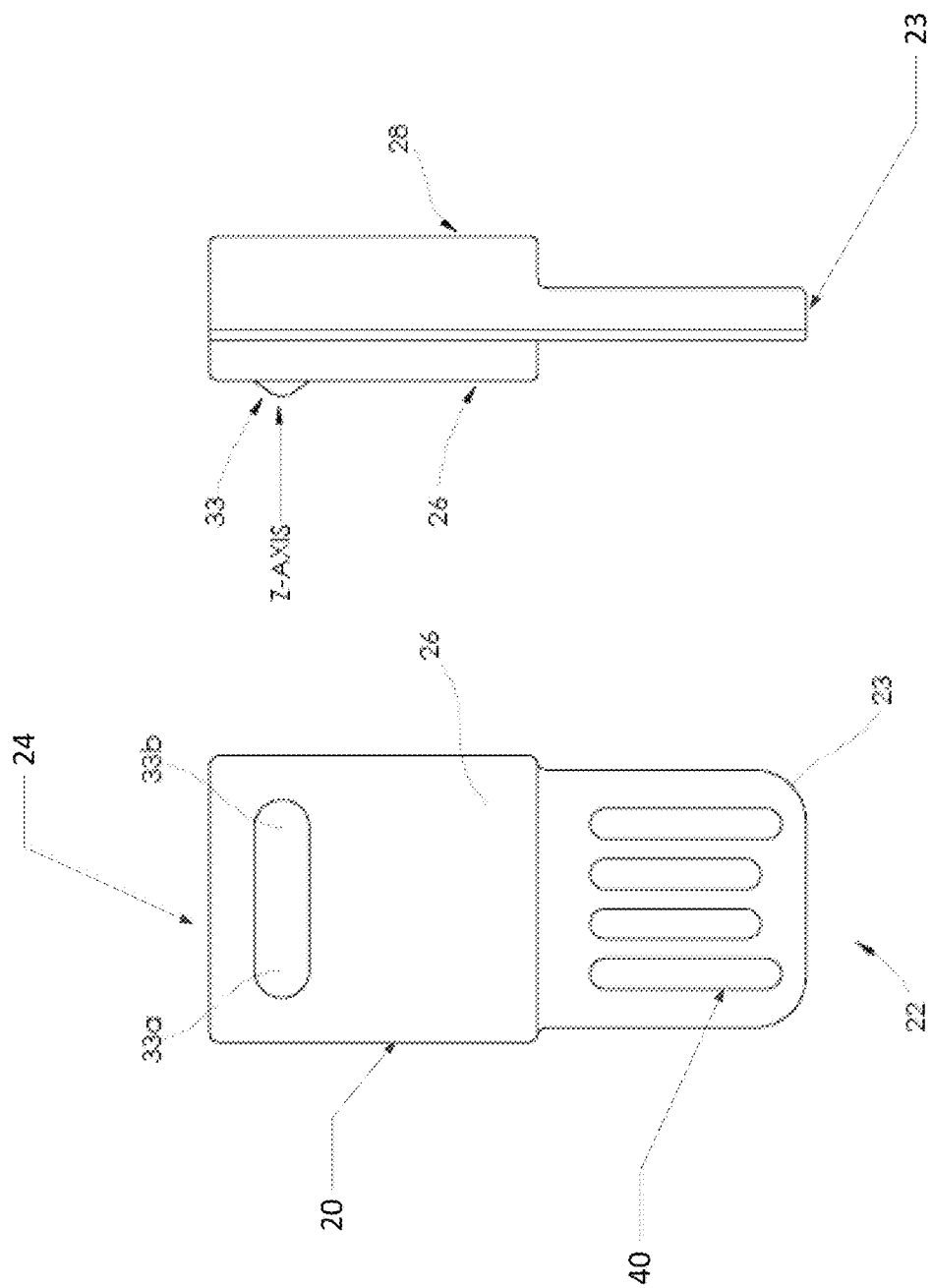

As illustrated in the example embodiment shown in FIGS. 7A-B, the USB device 16 has many features similar to a USB flash drive, but has additional functionality as discussed in greater detail below. Additionally, as shown in FIGS. 7A-D, in some aspects of the present disclosure, the housing 20 may include a first end 22, a second end 24, a top cover 26, and a bottom cover 28. General components and functional capabilities of the USB device 16 and controller 21 will be described in greater detail below.

Figure 8:
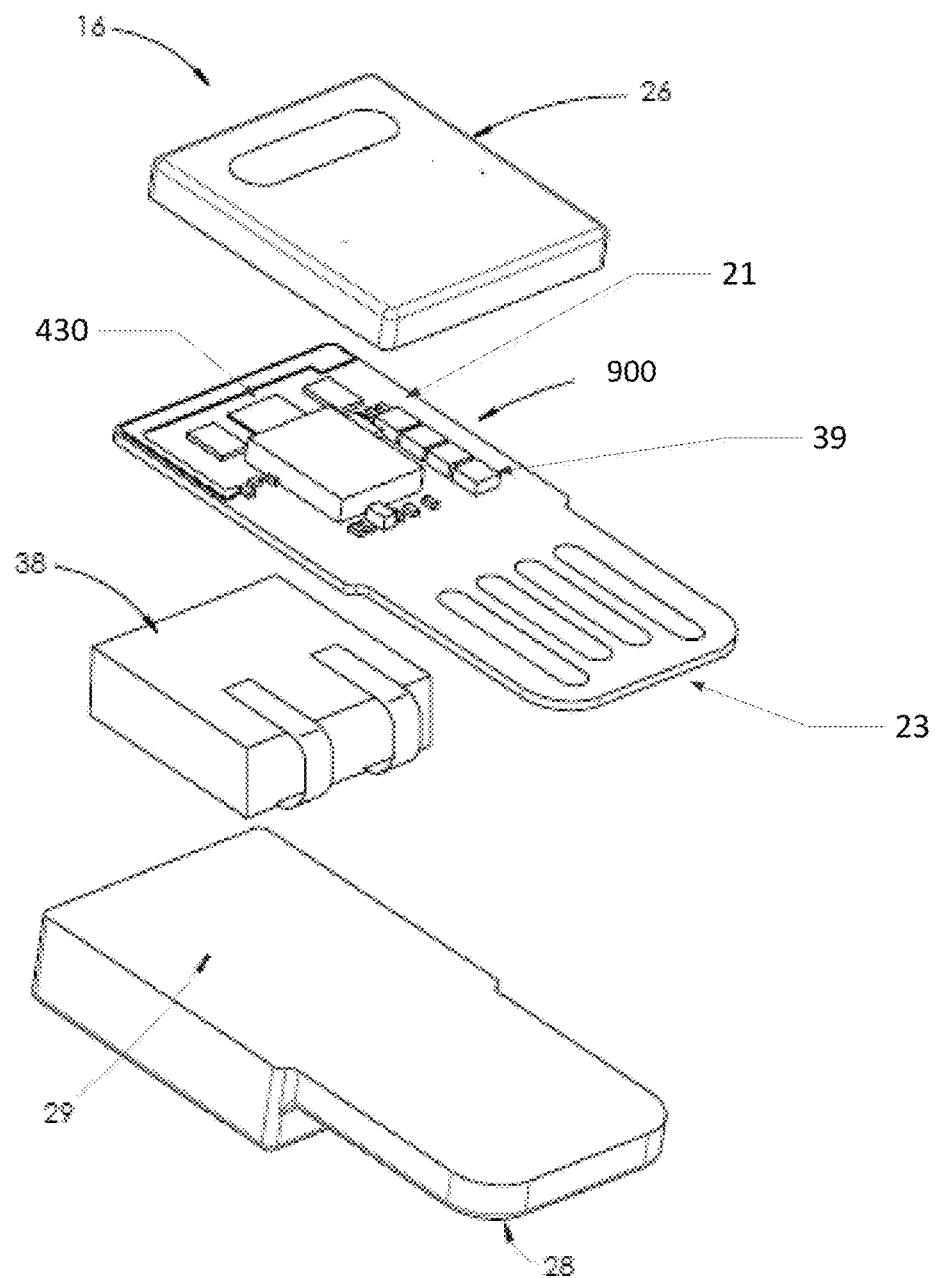
FIG. 8 is a perspective exploded view of the USB-type device as shown in FIG. 2A.

In some aspects of the present disclosure, as depicted in FIGS. 8 and 9A-B, the various components of the USB device may be supported by the housing 20, and said components may include a printed circuit board 900 of a controller 21, the controller having a suitable processor (e.g., processor 39) and other known components, a rechargeable power source 38, an input device assembly 430, an output device assembly 36, and a communication connector 23, which may be considered a part of the input device assembly 430 and/or the output device assembly 36 in various embodiments. The communication connector 23 may be, for instance, a USB connector 23. The controller 21 is operably connected to the input device assembly 430, the output device assembly 36, and the communication connector 23. In some aspects of the present disclosure, controller 23 may include one or more features of controller 404 as described above with respect to FIG. 4.

As further shown in the example embodiment shown in FIGS. 7B-C, the first end 22 includes a communication connector 23 that is generally illustrated as a standard USB connector having leads or contacts embedded therein. In some embodiments, the communication connector 23 may be integrally molded with the housing 20, or a component (e.g., controller 21) within the housing, as described in greater detail below. The communication connector 23 may be adapted such that a USB device 16 can be engaged with a USB hub of a device (e.g., a computer, wall charger, etc.) and/or a receiver (ancillary) member. The top cover 26 may include a pushbutton 33 that will cooperate with an input device assembly 430 of the controller 21 for controlling the USB device 16 as described in greater detail below. It is understood that the top cover 26 of the housing 20 could be formed such that it has, for example, a solid, thin layer and/or transparent or translucent components, wherein light emitted from a lighting element 437 (see e.g., FIG. 9A) is visible through the top cover 26.

In some embodiments, the USB device 16 may be removably connected to or engaged with a carrier (e.g., wristband, strap, etc.). In other embodiments, the USB device 16 may be removably connected to receiver member (e.g., a cap, closure member, etc.). In some of these embodiments, the USB device 16 and/or receiver member may be removably attached to an article of footwear, an article of apparel, a piece of athletic equipment, or any other suitable item (or carrier).

As will be described in greater detail below, in such arrangements, the receiver member may include an aperture (e.g., a female USB connector) for receiving a USB connector 23 of USB device 16. In other aspects of the present disclosure, the USB device 16 may be connected to and/or operatively engaged with a receiver member having both a male USB connector and a female USB connector, such that the receiver member may be engaged with a first USB device and further engaged with or operatively connected to an additional device (e.g., a receiver member, a second USB device, etc.) or item (e.g., article of footwear, piece of athletic equipment, etc. In further aspects of the present disclosure, the USB device 16 may be connected to and/or operatively engaged with a second USB device. In such arrangements, the second USB device may include a first end and a second end, wherein the first end includes a communication connector (e.g., a male USB connector), and the second end includes an aperture configured to receive a USB connector of a USB device (e.g., a female USB connector).

As further shown in the example embodiment depicted in FIG. 8, the components of the controller 21 are contained within and supported by the housing 20. The controller 21 includes various electronic components allowing the controller 21 and USB device 16 to act as an interface device wherein the device 16 can communicate with the sensor 12, record and store data relating to athletic performance, other time information, as well as upload performance data to a remote location or site as described in greater detail below. It is further understood that the controller 21 is operably connected to the connector 23 of the housing 20. As furthered illustrated in FIG. 8, the bottom cover 28 of the housing 20 may define a cavity 29 therein for accommodating various components of the USB device 16, such as the controller 21.

As further shown in the example embodiment depicted in FIG. 7D, the communication connector 23 may extend from the first end 22 of the housing 20. It is understood that the communication connector 23 could be positioned at various other locations of the housing 20. The communication connector 23 generally extends rigidly from the housing 20. As further shown in other embodiments, the communication connector 23 can be flexible with respect to the housing 20. In other embodiments described herein, the USB connector 23 may be rigidly connected to the housing 20 in other configurations. As discussed, the communication connector 23 is a USB connector and may have a plurality of leads therein and wherein the leads are operably connected to the controller 21. The housing 20 can be made from a variety of different rigid materials including metal or generally rigid polymeric materials. The housing 20 could also be formed in a two-shot injection molding process wherein the communication connector 23 could be molded to be flexible with respect to the housing 20.

It is also understood that the USB connector 23 could be separately fastened to the housing 20 consistent with other embodiments described herein. The USB connector 23 generally provides a water-resistant connection with the housing 20 and controller 21. Because the USB device 16 may be used in fitness activities, there is some chance that the USB device 16 can be subject to water or moisture such as perspiration. The housing 20 is designed to be water-resistant to protect components of the USB device such as controller 21 and rechargeable power source 38. Such structures further provide for a certain level of impact resistance.

Any desired system for releasably securing a first USB device with a receiver member (e.g., a closure member, a second USB device, etc.) may be used without departing from the present disclosure. For example, this securing system may include one or more members of the first USB device (e.g., connector 23) that extends into one or more openings, recesses, grooves, and/or discontinuities provided in a housing structure (e.g., the housing of the receiver member and/or the housing of a second USB device). As additional examples, the receiver member may optionally include a fastener element that engages with a portion of the housing 20 of the USB device 16. Adhesives and/or hook-and-loop type fastener arrangements also may be used to engage the receiver member with the USB device and/or to directly engage the USB device with the receiver member. As will be discussed in greater detail below, the securing system may be mechanically activated or operated, electronically activated or operated, and/or electromechanically activated and/or operated. In some aspects of the present disclosure, the receiver member may include a female USB connector for receiving connector 23 of USB device 16.

As further shown in the example embodiment depicted in FIG. 8, the controller 21 generally has a processor 39 that is operably connected to the input device assembly 430 as understood by those skilled in the art. The controller 21 includes software that in cooperation with the input device assembly provide user interface features as will be described in greater below. The components of the controller 21 are contained within and supported by the housing 20. The controller 21 includes various electronic components including a rechargeable power supply 38 (e.g., rechargeable battery or other battery types) and system memory. The controller 21 may also include an antenna 934, allowing the controller and USB device 16 to communicate with a computing device (e.g., an external sensor 12, a mobile device, etc.), and to record/store data relating to athletic performance, and other time information. As will be explained in more detail below, a variety of communication protocols may be utilized by the USB device and/or antenna 934 to transmit/receive data from a computing device. The controller 21 also functions to upload performance data to a remote location or site as is known in the art, but can also download additional information from a remote site or location to be stored by the controller 21 for further use. The antenna 934 can take various forms including a chip antenna associated with the controller 21. Alternatively, the antenna 934 could be a sheet metal antenna. The controller is operably connected to the communication connector 23 of the housing 20.

As shown in the example embodiment depicted in FIG. 9A, the controller 21 (and/or input device assembly 430) may include a transmission/reception system 937 configured for communication with a sensor (e.g., sensor 12), other USB devices, computing devices, mobile devices, or any other suitable electronic device/component using any type of known electronic communication, including contacted and contactless communication methods, such as RFID, Bluetooth, infrared transmission, cellular transmissions, etc. In some aspects of the present disclosure, antenna 934 may be included in transmission/reception system 937. The USB device 16 may be configured to communicate using short-range wireless transmission protocols (e.g., short-range RF transmission), long-range transmission protocols, wired transmission methods and/or combinations thereof. For example, short-range wireless methods may include BLUETOOTH wireless communication protocol, so that it can be employed with Bluetooth-capable mobile telephones, WiBree, personal digital assistants, watches or personal computers. WiBree generally refers to digital radio technology that provides short-range transceiver capabilities with low power consumption. In one or more arrangements, WiBree may complement other protocols such as Bluetooth. In other embodiments, the controller 21 (and/or input device assembly 430) may include a wireless data port, (e.g., a Bluetooth interface, a Wi-Fi interfaces, an infrared data port, or the like) to communicate with other computing devices, mobile devices, and/or electronic components (e.g., sensors). Of course, still other wireless or wired communication techniques could be employed by the USB device 16. In other aspects of the present disclosure, USB device 16 may be configured to have the same transmission capabilities of portable device 112, as described above with reference to FIG. 1.

As further shown in the example embodiment depicted in FIG. 8, the input device assembly 430 may include one or more input devices such as in the form of a depressible button(s). In certain exemplary embodiment, the USB connector 23 can also be considered an input device when data is transferred to a computing device (and/or receiver member) via the connector 23. In one exemplary embodiment, the input device assembly 430 may comprise a single input button 431 (see e.g., FIG. 9A). In other exemplary embodiments, the input device assembly 430 may be configured to include a plurality of buttons. The input button 431 may be located within a proximity to the top cover 26 of the housing 16. For example, the input button 431 may be located underneath the top cover 26, and between the top cover 26 and bottom cover 28 of the housing 20. The input button 431 may correspond with a first input and may be operably connected to the controller 21 for controlling the USB device 16, such as a printed circuit board of the controller. FIGS. 9A-B show schematic views of a printed circuit board of the controller 21. The controller 21 includes lead interfaces 440 that cooperate with the USB connector 23.

Referring now to the example embodiment depicted in FIG. 7D, the push button 33 is configured to operate in a z-axis direction. The user may activate the first input by actuating the input button 431. In some aspects of the present disclosure, the user may actuate the input button 431 by pressing on the push button 33 on the top cover 26 of the housing 20. The user may squeeze the push button 33 and the opposite bottom cover 28 of the housing 20 to actuate input button 431. In some aspects of the present disclosure, the input button 431 may also cooperate with an additional input of the controller 21 for controlling the USB device 16. For example, a user may press one segment of the push button 33, such as a first side segment 33a, for a first input, and may press a second segment of the push button 33, such as a second side segment 33b, for a second or additional input different from the first input. It is also understood that the push button 33 may be positioned on the bottom cover 28 of the housing 20.

As further shown in the example embodiment depicted in FIG. 9A, the USB device may include one or more lighting elements 437. In some aspects of the present disclosure, indicator system 438 of USB device 16 may comprise one or more lighting elements 437. The USB connector 23 may also be considered an output device when transferring data from the USB device 16. The controller 21 can have additional capabilities for communicating with other devices such as other, USB devices, sensors, or other electronic devices.

Figure 14:
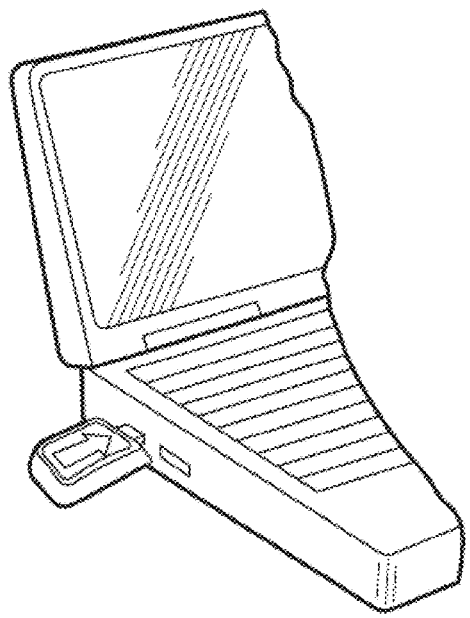
FIG. 14 is a perspective view of a USB-type device engaged with a computing device according to one or more aspects of the present disclosure.

The USB device 16 has a rechargeable battery 38 contained within the housing to provide power to the USB device 16 and/or any other operatively connected devices (e.g., a receiver member). The rechargeable battery may be charged such as when the user plugs the USB device 16 into a computer as shown in the example embodiment depicted in FIG. 14. Additionally or alternatively, the rechargeable battery may be charged such as when the user engages a receiver member (e.g., a closure member) having an independent power supply with the USB device 16. It is understood that the battery associated with the controller can utilize one or more batteries or power sources. A first battery may be utilized for the general USB device functions. A second battery may be utilized for other controller functions including communicating with other devices or sensors for example. The first battery would be a typical battery that has a long life and support the basic USB device functions. The second battery can be a traditional rechargeable battery to support the additional controller functions associated with monitoring athletic performance, which functions may be more demanding on the power source. In such configuration, the USB device functions would not be compromised even if the rechargeable battery was depleted by the athletic performance monitoring functions or if the user had not worked out for some time and had not charged the USB device 16. In other aspects of the disclosure, a single battery may be utilized to support the basic USB device functions as well as any additional controller functions associated with monitoring athletic performance. In such configurations, the battery can be a traditional rechargeable battery. In some aspects of the present disclosure, the USB device may be configured to report a power supply level (or remaining power capacity) of a power supply source. For example, the USB device may be configured to report a current power supply level for rechargeable battery 38. In such arrangements, the USB device may transmit data indicating the remaining power capacity to a remote system or other suitable computing device.

The example embodiment illustrated in FIG. 9A depicts the communication connector 23 in greater detail. In this embodiment, the communication connector 424 is in operable communication with the controller 21. As discussed, the communication connector 23 is in the form of a USB connector 23. As shown in the example embodiment depicted in FIG. 9A, the controller 21 may include lead interfaces 440 that cooperate with the USB connector 23. In a further exemplary embodiment the leads 440 are resilient members such as in the form of wire springs. The USB connector 23 is easily inserted into the user's computer for data transfer as described above (FIG. 14). This USB connector design provides a secure and robust connection between the connector and the housing. This construction also minimizes the chance of moisture entering the housing via this connection.

As discussed above, the USB device 16 may include an input device assembly 430 having one or more buttons operably connected to the controller 21 for controlling the USB device 16. The user may activate input by actuating an input button (e.g., input button 431) in a variety of manners. In some aspects of the present disclosure, the user may actuate the input button 431 by pressing on the push button 33 on the top cover 26 of the housing 20 of the USB device 16. In other aspects of the present disclosure, based on input (or activity) sensed by the USB device 16, the controller 21 may illuminate one or more lighting elements 437. There are a variety of ways in which the lighting elements may be illuminated without departing from the scope of the present disclosure, such as by fading on, periodically blinking on and off, and the like. As another example, one or more of the lighting elements 437 may be activated (e.g., blink on and off, fade on, etc.) to indicate an operation of the USB device. Additionally, the color of the illuminated lighting members may further indicate particular information sensed by the USB device (e.g., the type of input and/or activity sensed by the USB device).

Depressing a button of USB device 16 (e.g., pushbutton 33) may activate one or more functions on the USB device 16. A "short press" may correspond to the action of briefly depressing an input button for some predetermined threshold amount of time. For example, a short press may correspond to the action of depressing the input button for greater than 0.25 seconds, but no longer than 1.5 seconds. A "long press" may correspond to the action of depressing the input button and then holding that input button in the depressed position for some predetermined threshold period of time, e.g., greater than 1.5 seconds. Those skilled in the art will realize that mechanical user interface devices are not required and that one or more user interfaces may comprise "soft" buttons or the like which are dynamically displayed, for example, on a touchscreen display.

In some aspects of the present disclosure, when the USB device 16 is powered off, a long press of button 33 may cause the USB device 16 to power on. Based on input (or activity) sensed by the USB device 16, the controller 21 may illuminate one or more lighting elements 437 on the indicator system 438. Additionally or alternatively, the color of the illuminated lighting elements may vary based on a level of power (or charge) remaining in the power supply (e.g., battery 38) for USB device 16. For example, in some arrangements, when the USB device 16 is powered on with a remaining power supply of greater than or equal to 50%, one or more lighting elements 437 may fade on and be illuminated in green to indicate that the USB device has powered on and has a threshold amount of power remaining in battery 38. Additionally or alternatively, when the USB device 16 is powered on with a remaining power supply of less than 50%, one or more lighting elements 437 may fade on and be illuminated in red.

In other aspects of the disclosure, when the USB device is powered on, briefly depressing button 33 may cause the USB device to initiate a performance monitoring session, allowing the user to monitor and record various physical and/or physiological characteristics of the wearer or other performance data. In this example, one or more of the lighting elements 437 may be blink on and off (e.g., illuminated for a first threshold period of time (e.g., 100 ms) and then remain off for a second threshold period of time (e.g., 300 ms)) a predetermined number of times to indicate that the USB device has initiated a performance monitoring session.

In some aspects of the disclosure, one or more of the lighting elements 437 may be illuminated for a threshold period of time (e.g., 100 ms) and then remain off for a second threshold period of time (e.g., 5 seconds) while the USB device is in a performance monitoring session. In some arrangements, when the USB device 16 is in a performance monitoring session, one or more lighting elements 437 may be illuminated in green to indicate the USB device has a remaining power supply greater than or equal to 20%. Additionally or alternatively, during a performance monitoring session, one or more lighting elements 437 may be illuminated in red to indicate the USB device has a remaining power supply less than 20%.

In other aspects of the disclosure, during a performance monitoring session, briefly pressing button 33 may cause the USB device to end the performance monitoring session. In such arrangements, one or more of the lighting elements 437 may be illuminated for a threshold period of time (e.g., 300 ms) to indicate the end of the performance monitoring session. In other aspects of the disclosure, when the USB device 16 is engaged with a USB port of a computing device, one or more of the lighting elements 437 maybe illuminated red and blink on and off (e.g., illuminated for a first threshold period of time (e.g., 300 ms) and then remain off for a second threshold period of time (e.g., 700 ms)) continuously to indicate that the battery 38 of the USB device 16 is recharging and that the remaining power supply is less than 90%. In other examples, when the USB device 16 is engaged with a USB port of a computing device, one or more of the lighting elements 437 may be continuously illuminated green to indicate that the battery 38 of the USB device 16 is charged (and/or is recharging) and that the remaining power supply is greater than or equal to 90%.

In other aspects of the disclosure, as will be explained in further detail below, systems and methods in accordance with at least some examples of the present disclosure may be used in conjunction with software applications to control USB devices, to review performance data recorded by USB devices and/or other devices, and the like. When a software application running on a computing device attempts to communicate with USB device 16 (e.g., via Bluetooth or any other suitable communication method), one or more of the lighting elements 437 may be illuminated blue and may blink on and off (e.g., illuminated for a first threshold period of time (e.g., 200 ms) and then remain off for a second threshold period of time (e.g., 300 ms)) for a predetermined number of times (e.g., six times) to indicate that an electronic device is attempting to communicate (e.g., establishing a pairing relationship) with the USB device. Various other types of devices may attempt to establish a communication relationship with a USB device, such as a sensor, another USB device, and the like.

In some embodiment, one or more of the lighting elements 437 may be continuously illuminated red to indicate that the remaining power supply for USB device 16 is below 5%. In another embodiment, one or more of the lighting elements 437 may be continuously illuminated yellow to indicate that the memory for USB device has exceeded a threshold capacity. In such arrangements, the USB device may no longer record additional performance data upon the memory for the USB device exceeding the memory threshold capacity. In other aspects of the disclosure, when the USB device is powered on, a long press of button 33 may cause the USB device to power off. In such arrangements, one or more of the lighting elements 437 may fade off over a threshold period of time (e.g., 1 second) to indicate the USB device is powering off.

Referring now to the example embodiment depicted in FIG. 9B, in some aspects of the present disclosure, output assembly 36 may include battery contacts 450, test points 451 and a device component area 452. In some embodiments, battery contacts 450 are configured to receive a battery (or other suitable power supply) from an external device (e.g., a receiver member, a second USB device, etc.) and may be further configured to draw power from the battery and convert the voltage input to a charger output for purposes of recharging battery 38. For example, a first battery may be provided in a first receiver member engaged with USB device 16. Battery contacts 450 may be configured to draw power from the first battery to recharge battery 38. In other aspects of the present disclosure, output assembly 36 may include integrally molded test point socket 453 configured to provide fault current or voltage loss monitoring of a conductor within USB device 16. Additionally, test points 451 may be configured to measure a termination voltage of a communication link within USB device 16. In some aspects of the present disclosure an electronic device, such as a sensor or other suitable electronic component, may be located in component area 452 of output assembly 36.

Figure 10A:
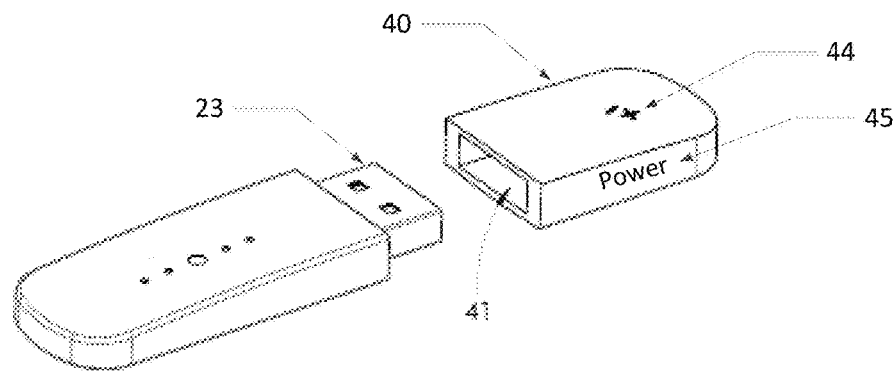
FIGS. 10A-C are perspective views of a USB-type device and corresponding receiver member for the USB-type device according to one or more aspects of the present disclosure.
Figure 10B:
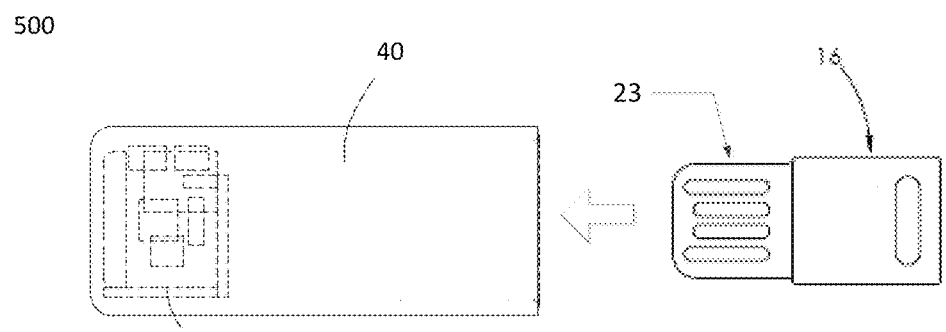

As discussed above, and as illustrated in the example embodiments depicted in FIGS. 10A-B, a receiver member (e.g., closure member 40) may be removably engaged with USB device 16. The USB device 16 may be configured to operate with a plurality of different receiver member. In some aspects of the disclosure, when engaged with the USB device 16, the receiver member 40 may provide the USB device 16 with additional functionality and/or operational features. As will be explained in more detail below, in such arrangements, the receiver member 40 may include one or more electronic modules 42, components, sensors, or other electronic devices configured to operate with and provide additional monitoring functionality and/or operational features to the USB device 16. In some aspects of the present disclosure, USB device 16 may include a sensor device or other electronic components configured to collect performance data. Additionally or alternatively, the receiver member 40 may include a rechargeable battery configured to supply power to the electronic module 42 of the receiver member 40, to supply power to the USB device 16 and/or to recharge battery 38 of USB device 16.

As shown in the example embodiment depicted in FIG. 10A, the receiver member 40 may have an aperture 41 (or receptacle 41) dimensioned to receive the communication connector 23 of the USB device 16. In some embodiments, the aperture 41 may include a female USB connector. In some aspects of the present disclosure, the receiver member 40 may include therein an electronic device 42. A receiver member may include one or more electronic devices (e.g., sensors) that are configured to provide the USB device 16 with additional monitoring capabilities and/or operational features, such as geospace seismic recorder features (GSR), altitude monitoring, temperature/humidity monitoring, WI-FI communications, NFC communications, Bluetooth communications, near IR spectroscopy, and the like. For example, a receiver member may include an electronic device configured to provide the USB device with global positioning system ("GPS") features. The electronic device may have various electronic components including a power supply, magnetic sensor elements, microprocessor, memory transmission system, and other suitable electronic components. The electronic device may be used in conjunction with other components of the system to record and monitor various types of performance data and other information. For instance, referring back to the example above, the receiver member may include therein a GPS receiver, and may be further configured to transmit location data collected by the GPS receiver to a remote system or other suitable computing device.

As another example, a receiver member may include therein one or more sensors (e.g., accelerometer, gyroscope, altimeter, thermometer, magnetometer, IR sensor, etc.) to record and monitor athletic performance of a user. The one or more sensors of the receiver member may take various forms. For example, a sensor included within a receiver member 40, such as an accelerometer, may be used in conjunction with other electronic components to record speed and distance among other parameters of athletic performance. In one example, the accelerometer may be used in conjunction with a transmission system to transmit activity data collected by the accelerometer to a remote system or other suitable computing device. It is understood that the accelerometer could be a three-axis accelerometer and have additional function in addition to sensing a speed and/or a distance traveled by a user. For example, the accelerometer could be used to wake-up the USB device upon motion as well as speed and distance measurement for the user.

At least some systems and methods in accordance with aspects of the present disclosure may include one or more types of sensors for detecting a user's orientation or mode of moving during an athletic performance. For example, if desired, an electronic compass or a rotational sensor may be incorporated into the performance monitoring system, e.g., to aid in detecting an athlete's direction of movement and/or to provide additional details regarding the characteristics of the athlete's mode of movement (e.g., running forward, running at a side step, running backward, etc.). In some embodiments, sensor 12, (e.g., accelerometer) can also provide useful information regarding the direction of movement, if the sensor has a predetermined orientation at the start (e.g., with one axis of a two or three axis accelerometer facing the forward direction of motion). A determination of the amount of time or distance that an athlete runs forward, sideways, or backward could be a useful metric for measuring performance, at least in some sports.

In other aspects of the present disclosure, various algorithms may be utilized to control the measurement of performance data by the USB device 16 (or other electronic component). For example, if desired, different pedometer based speed and distance determination algorithms may be used, depending on the athlete's mode of movement (forward, backward, sideways, etc.), which may enable a more accurate determination of the athlete's overall movement speed or movement distance. More specifically, one algorithm may be appropriate for determining speed or distance (e.g., based on foot loft time, etc.) when an athlete is running forward, but a different algorithm may be more appropriate when running sideways, and even a different algorithm may more appropriate (e.g., generate more accurate results) when running backward. In other aspects of the present disclosure, the processor 39 of USB device 16 may be programmed, configured and/or adapted to use particular algorithms when monitoring, sensing, or recording performance data.

As noted above, USB device 16 may include one or more electronic components (e.g., sensors) for measuring a user's athletic performance. In some aspects of the disclosure, one or more different receiver member may respectively include an electronic device/component configured to provide the USB device 16 with additional operational features and functions. Thus, a user may easily modify the operational features and/or monitoring capabilities of a first USB device by engaging a receiver member with the first USB device. For example, if a user desires for USB device 16 to monitor the location of a wearer of the USB device, the user may engage the USB device 16 with a first receiver member that provides GPS functionality and/or features (e.g., a first receiver member that includes a GPS sensor 42 therein). Additionally or alternatively, if the user desires for the USB device 16 to monitor the heart rate of the wearer, the user may replace the first receiver member with a second receiver member that includes an electronic device/component therein configured to measure the heart rate of the wearer (e.g., a heart-rate monitor). Accordingly, by engaging the USB device 16 with an appropriate receiver member 40, a user may configure the USB device to monitor and/or record a particular physical and/or physiological characteristic of the wearer.

In some aspects of the present disclosure, as noted above, a receiver member may be equipped with a USB connector such that a second receiver member (e.g., closure member, USB device) may be engaged therewith. In such arrangements, the second receiver member may provide the first USB device with additional operational functions. Referring back to the example above, in this example, the user may engage the USB device 16 with a first receiver member configured to provide GPS functionality, and then engage the first receiver member with a second receiver member (e.g., closure member, second USB device, etc.) configured to measure the heart rate and body temperature of the wearer. Accordingly, the resulting assembly of the USB device 16, first receiver member, and second receiver member, may provide the USB device 16 with additional performance monitoring capabilities that the device 16 may not otherwise have on its own. Additionally or alternatively, a third receiver member may be attached to the resulting device assembly, wherein the third receiver member (e.g., closure member) includes an additional power supply for USB device 16 and/or any of the receiver members. As will be noted, the USB device 16, in some arrangements, may be configured to include the various electronic components discussed above without engaging additional USB devices and/or receiver member.

In some aspects of the present disclosure, the surface of a housing for a receiver member may include a symbol, graphic image, text, or other suitable indicator to indicate (or identify) the various operational features or monitoring capabilities provided by the one or more electronic components included therein. For example, the top cover 26 of housing 20 for USB device 16 may include an indicia thereon to indicate the various monitoring features or capabilities available for device 16. For example, as shown in FIG. 10A, the housing of receiver member includes a first indicia 44 indicating that the receiver member includes an additional power supply for USB device 16, as represented by the symbols "+" and "−" symbol shown on the housing. Additionally, the housing of receiver member includes a second indicia 45 on the housing comprising the test "Power." As will be appreciated, the indicia may be located in any suitable location on the surface of the housing such that the indicia is visually perceptible by a user. As another example, the surface of a housing for receiver member 40 may include an indicia thereon to indicate the various monitoring features or capabilities provided by the receiver member. As noted above, the indicia can take various forms including wording, graphics, color schemes, textures, or other designs etc.

Additionally, in some aspects of the present disclosure, an electronic module (e.g., sensor 42) may be a component of a larger performance monitoring system, and may communicate with one or more other electronic devices (e.g., USB devices, sensors, etc.) in a performance monitoring system, as shown in FIG. 1. For example, the USB device 16 worn by a user may communicate with a shoe sensor 12 and/or any other sensor and/or or USB device assembly (not shown) worn by the user. The USB device 16 may further communicate with only one of the shoe sensor and other USB device assemblies worn by a user depending on the user's preference.

Figure 10C:
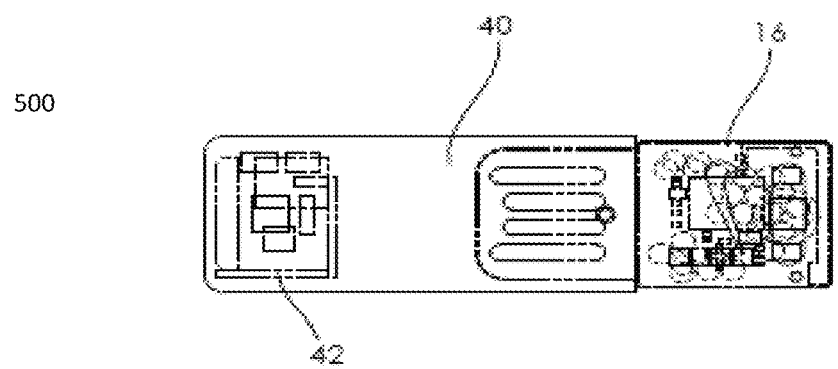

FIGS. 10B and 10C illustrate example views of device assembly 500. In particular, FIG. 10B illustrates a view of device assembly 500 wherein the USB device 16 is not engaged with receiver member 40. FIG. 10C illustrates an example view of device assembly 500 wherein the USB device 16 is engaged with receiver member 40 such that the connector 23 of USB device 16 fits into the opening or recess 41 provided in the receiver member 40, as shown in the example embodiment depicted in FIG. 10A. In some instances, the receiver member 40 may include therein an electronic module 42, e.g., of the various types described above (such as accelerometer 42). In other instances, the receiver member may include a rechargeable power source (e.g., a battery). A wide variety of different receiver member 40 may be configured to engage with connector 23 of USB device 16 without departing from the present disclosure. For example, as described above in conjunction with the example embodiments depicted in FIGS. 10B-C, the element 42 of receiver member 40 may constitute an electronic module (e.g., module 42) for measuring a physical and/or physiological parameter associated with use of the USB device 16, with use of an article of footwear (or apparel) and/or a piece of athletic equipment with which the USB device 16 is operatively connected or encaged, or with use of other sensors, electronic devices and/or components for various other uses, including, for example, communicating with other USB devices of a performance monitoring system (e.g., performance monitoring system 610).

As discussed above, if desired, different electronic devices may be included within different receiver member s configured to communicate and/or be engaged with USB device 16, and these devices may provide information relating to the same or different physical and/or physiological parameters, may be used to provide the same or different types of information to a remote system, may be used to provide information for controlling the same or different external devices, may provide different combinations of information and functions, etc. In this manner, if desired, a broader scope of functions may be performed and/or information may be provided to the user or others, and/or more reliable and/or redundant data or information may be made available during the course of the performance.

Figure 11A:
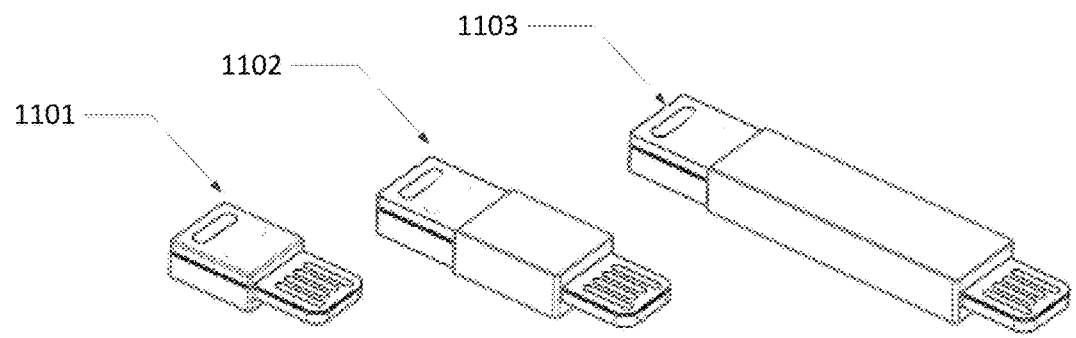
FIG. 11A is a perspective view of USB-type devices according to one or more aspects of the present disclosure.
Figure 11B:
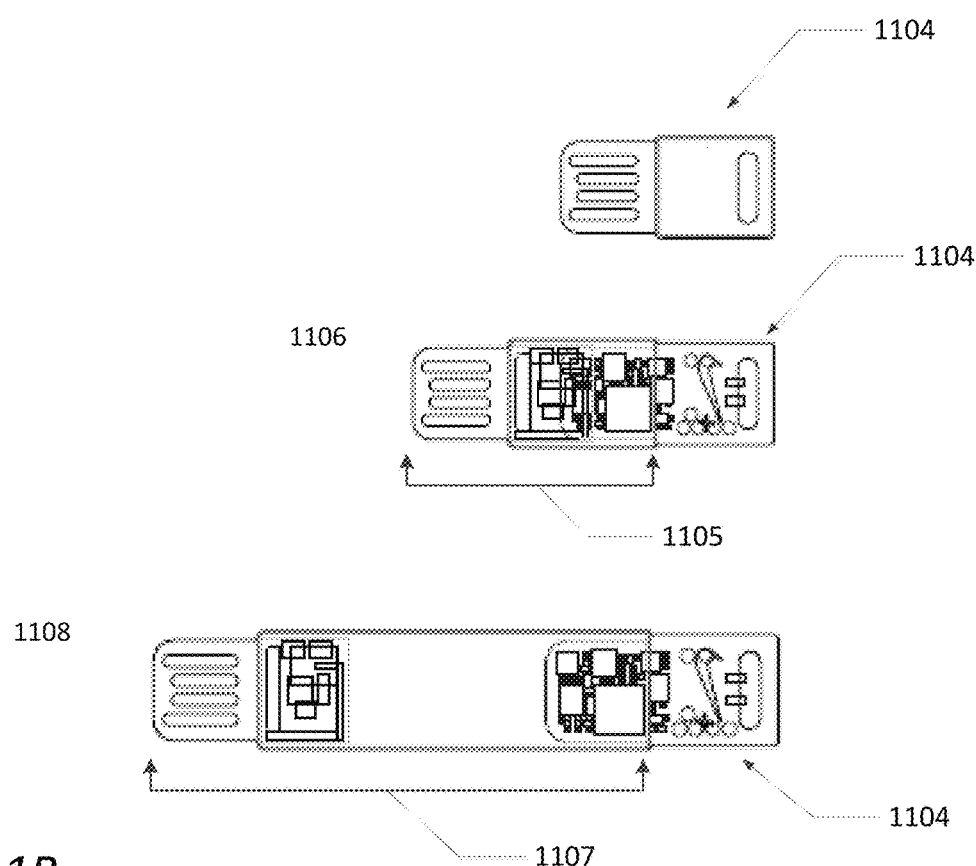
FIG. 11B is a top plan view of the USB-type devices as shown in FIG. 11A.

As shown in the example embodiments depicted in FIGS. 11A-B, the USB device 16 and/or receiver member 40 may be manufactured in a variety of different shapes or size. For example, FIG. 11A illustrates three different USB devices of varying sizes (see e.g., elements 1101-1103). The size or shape of the USB device (and/or a resulting USB device assembly) may vary for a variety of reasons with departing from the scope of the present disclosure. For example, the size/shape of the USB device may vary such that the USB device may more easily be engaged with and/or attached to an item. As another example, certain types of items, such as large athletic equipment, footwear, and the like, may demand larger and/or more durable USB devices; while other types of items, such as articles of apparel, wrist worn devices, and the like, may demand smaller USB devices. Additionally or alternatively, the size/shape of the USB device may vary such that the device is less (or more) visually perceptible to the wearer or third parties.

In some aspects of the present disclosure, the size/shape of a USB device (and/or a resulting USB device assembly) may depend on the number of additional receiver member or USB devices that have been connected together. Referring now to the example embodiment depicted in FIG. 11B, element 1104 illustrates a first (stand-alone) USB device. In one example, a first USB device 1104 may be engaged with a receiver member 1105 (e.g., second USB device 1105), the receiver member having both a female and male USB connector, thus resulting in USB device assembly 1106. In another example, the first USB device 1104 may be engaged with a receiver member 1107 (e.g., second USB device 1107), the receiver member having both a female and male USB connector, thus resulting in USB device assembly 1108. As shown in FIG. 11B, receiver member 1105 is larger in size than receiver member 1107, and as such device assembly 1106 is larger than device assembly 1108. As noted above, USB devices as described herein and/or receiver member may be manufactured in many different sizes to meet the various needs and desires of the wearer (or user). As previously discussed, and as illustrated in FIG. 11B, in some example embodiments a first USB (e.g., USB device 1104) device may be connected to and/or engaged with a receiver member (e.g., second USB devices 1105, 1107) that includes various electronic components providing additional monitoring/communications functionality, such that the resulting device assembly (e.g., device assembly 1106, 1108) has additional operational features and/or functionality than the initial stand-alone USB device (e.g., device 1104).

Figure 12A:
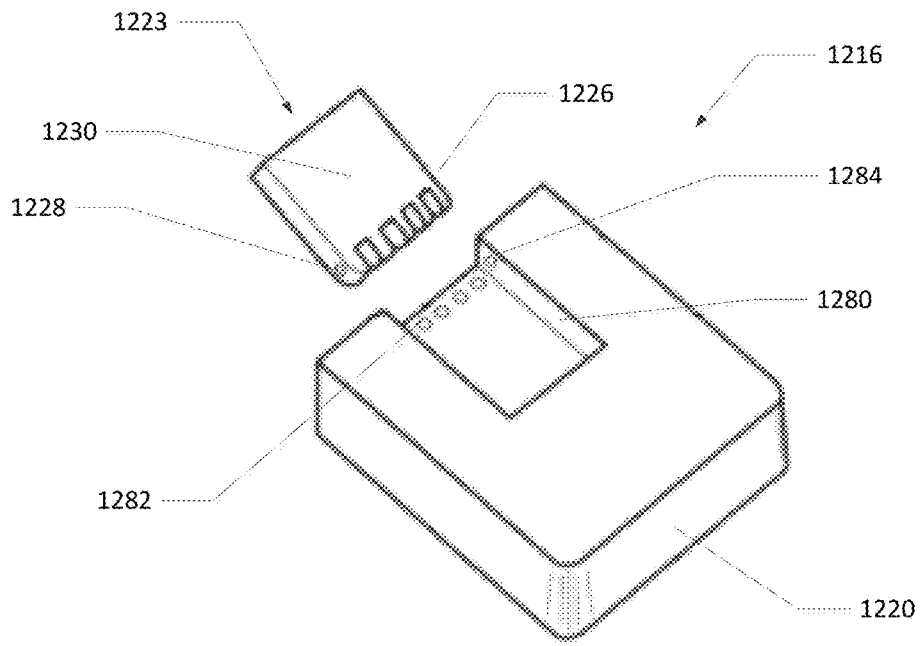
FIGS. 12A-C are perspective views of a USB-type device according to one or more aspects of the present disclosure.
Figure 12B:
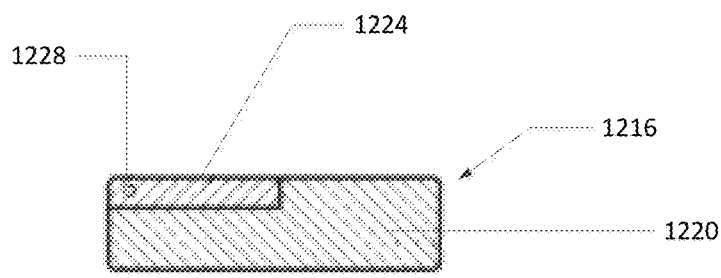
Figure 12C:
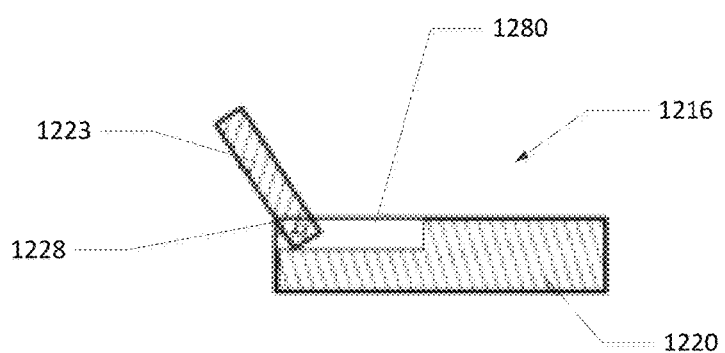

FIGS. 12A-C disclose example embodiment of the USB device generally designated with the reference numeral 716. This embodiment has a USB connector 1223 integrated with the housing 1220 of the USB device 1216. The USB device 1216 has a slot 1280 positioned in the bottom portion of the housing 1220. The slot 1280 has an opening 1282 in which two protrusions 1284 extend from each side of the opening 1282. The USB connector 1223 has a base 1226 that is pivotally or hingedly connected to the housing 1220 of the USB device 1216 with the protrusions 1284 connected to two holes 1228 on each side of the USB connector 1223. Additionally, in another embodiment, it should be understood that the housing 1220 may include the two holes 1228 on each side of the opening 1282 and the USB connector 1223 may include the protrusions 1284 which connect to the two holes 1228 on the housing 1220 of the USB device 1216. The USB connector 1223 has a distal end 1230 extending from the base 1226 that supports the leads that make up the USB connection 1223.

To transfer data, the user pivots the USB connector 1223 about the pivotal connection wherein the distal end 1230 of the USB connector 723 extends generally transversely from the USB device 1216. The USB connector 1223 can then be connected to a USB port of a computer as described above. Once data transfer is complete, the USB connector 1223 is removed from the computer and the USB connector 1223 is pivoted back into the slot 1280 of the housing 1220 as shown in the example embodiment depicted in FIG. 12B wherein the USB connector 1223 is completely contained within the housing 1220. It is understood that the distal end 1230 of the USB connector 1223 may have a gripping member thereon wherein a user could grasp the USB connector 1223 with a finger to pivot. The gripping member could take various forms such as a small protrusion or textured surface. It is further contemplated that a magnetic connection could be used between the housing 1220 and USB connector 1223 wherein the USB connector 1223 could be pushed further into the housing 1220 such that the USB connector 1223 would be then be forced back partially out of the housing 1220 where the USB connector 1223 could then be further pivoted out of the housing 1220. Operation of the USB device is identical as described above.

Figure 13A:
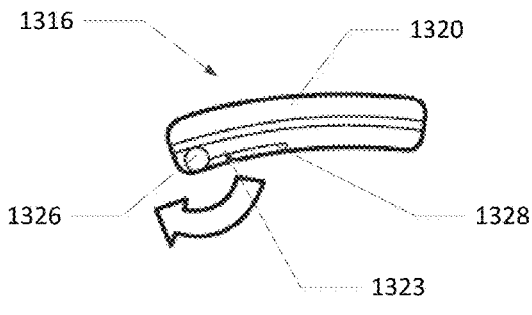
FIGS. 13A-B are perspective views of a USB-type device according to one or more aspects of the present disclosure.
Figure 13B:
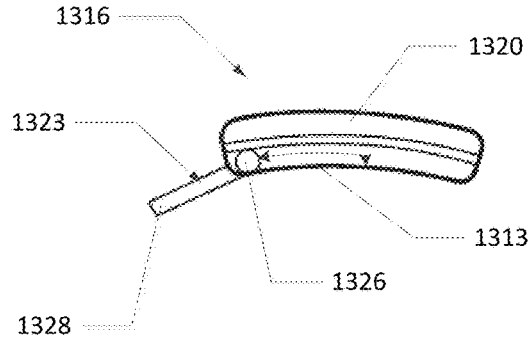

FIGS. 13A-B disclose another embodiment of the USB device generally designated with the reference numeral 816. This embodiment has a USB connector 1323 integrated with the housing 1320 of the USB device 1316. The USB device 1316 may have a slot 1313 positioned in the bottom portion of the housing 1320. The USB connector 1323 has a base 1326 that is pivotally or hingedly connected to the housing 1320 of the USB device 1316. The USB connector 1323 has a distal end 1328 extending from the base 1326 that supports to the leads that make up the USB connection 1323. To transfer data, the user pivots the USB connector 1323 about the pivotal connection wherein the distal end 1328 of the USB connector 1323 extends generally transversely from the USB device 1316 as shown in FIG. 13B. The USB connector 1323 can then be connected to a USB port of a computer as described above. Operation of the USB device 1316 is identical as described above.

FIGS. 15A-C illustrate exemplary mounting and clasp arrangements for the wearable device assembly described herein. The embodiment generally utilizes a USB type device (e.g., USB device 16) and a carrier. Similar reference numerals in sequential series may be used and additional features will be discussed below. The functionality of the USB device of the various embodiments is generally the same as discussed above and can be used in athletic performance monitoring system 610. In FIG. 15A, another embodiment of the wearable device assembly 14 is depicted. The wearable device assembly 14 generally includes a wearable device 16 that in one exemplary embodiment is a USB device (e.g., USB device 1516), and a carrier that in one exemplary embodiment takes the form of a wristband 1518. The USB device 1516 has many features similar to a USB flash drive, but has additional functionality as discussed above with respect to USB device 16. In some embodiments, the USB device 1516 is removably connected to a carrier (e.g., wristband 1518). The USB device 1516 has one end connected to a first end of the wristband 1518. The connector 1523 of USB device 1516 is inserted into a receiver member 1540 connected to a second end of the wristband 1518. To expose the connector 1523, the USB device 1516 is pulled from the receiver member 1540 as shown in the example embodiment depicted in FIG. 15A. It is understood that the carrier 1518 has appropriate structure for securing the band 1518 around the wrist (or other appendage) of the user. The wristband 1518 may have two pin arrangements, traditional watch straps, or straps utilizing hook and loop fasteners. The carrier 1518 can also be made of rubber or harder but flexible plastics. The plastic embodiments could also have co-molded components as well as plastics co-molded over fabric materials. It is understood that the devices and wristbands may have one or more of the connecting structures as discussed above.

It is further understood that the wearable device assembly can take other forms wherein other carriers are provided. As illustrated in the example embodiment depicted in FIG. 15B, the wearable device 1516 has a flange portion 1541 extending from a bottom cover of the housing for connecting the flange portion 1541 to the carrier 1519. A carrier may take various forms and shapes, and as illustrated in FIG. 15B, carrier 1519 is in the form of a clasp/clip 1552. In some embodiments, a portion of the carrier 1519 can have guide holes or a textured surface to provide for a tactile feel. The elongated slot 1547 receives the flange portion 1541 of the device 1516.

As shown in the example embodiment depicted in FIG. 15C, to secure the device 1516 to the carrier 1518, the flange portion 1541 is aligned with the elongated slot 1547 located in the carrier 1519. Once the flange portion 1541 is aligned with the elongated slot 1547, the flange portion 1541 is inserted through the slot 1547. The user then rotates the wearable device 1516 one hundred eighty degrees such that the first end and the second end of the flange portion 1541 align with a locking groove 1548.

As discussed above, the carrier 1519 of the USB device 1516 can be formed in a clip 1552. In such an arrangement, the USB device 1516 is similar in structure and operation to the wearable device assembly shown and described in embodiments having a cooperating slot and flange. The clip 1552 includes a first portion 1554, a second portion 1556, and a spring member 1558. The spring member 1558 biases the first portion 1554 and the second portion 1556 together. The first portion 1554 includes a slot 1547 that receives a flange 1541 on and/or connected to the USB device 1516. The USB device 1516 is mounted to the clip 1552 in a similar fashion as described above. The clip 1552 can be clipped to the user's apparel, otherwise on the person, as well as other locations or on other items (e.g., an article of footwear, a piece of equipment, and the like).

Figure 16A:
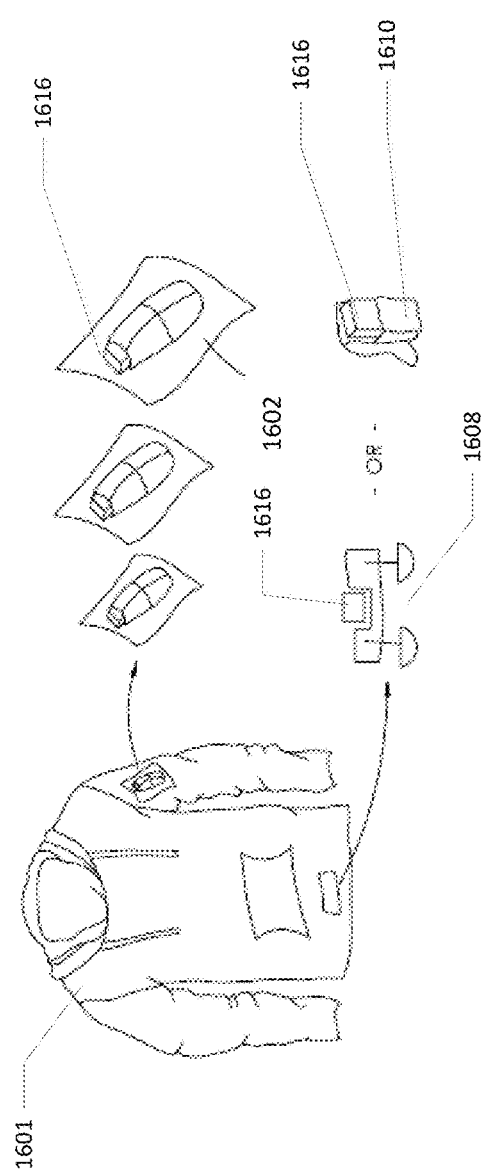
FIGS. 16A-B are perspective views of a wearable device assembly according to one or more aspects of the present disclosure.
Figure 16B:
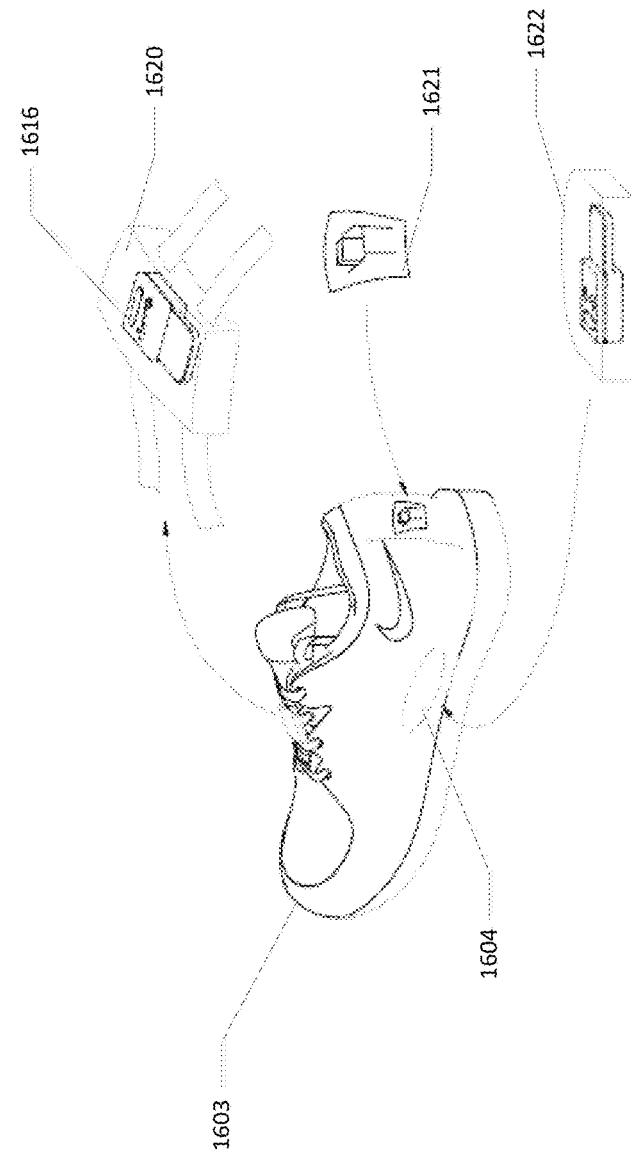

FIGS. 16A-B depict additional mounting arrangements of the wearable device assembly of the present disclosure. As illustrated in the example embodiments depicted in FIGS. 16A-B, a USB device and/or device assembly as described herein may be attached to an article of apparel (FIG. 16A) and/or an article of equipment (FIG. 16B). Various known methods and/or structures may be utilized to secure the USB device and/or device assembly to an article of apparel without departing from the scope of the present disclosure. For example, as depicted in FIG. 16A, the device assembly 1616 may be placed within a portion 1602 (e.g., pocket 1602) of an article of apparel 1601 to securely hold the device assembly 1616 in place during an athletic performance of the wearer of apparel 1601. As another example, the device assembly 1616 may be held in place by a clasp arrangement, as described above with respect to FIGS. 15B-C. As yet another example, the device assembly 1616 may be secured to article of apparel 1601 using one or more pins (e.g., element 1608). As another example, the location of the device could be in a plastic housing 1610 attached to the article of apparel 1601. As will be appreciated, the device assembly 1616 may also be placed (or secured) to any other desired location on apparel 1601. As depicted in FIG. 16B, the device assembly 1616 may be placed in a carrier (e.g., elements 1620) and then attached to a portion of the article of footwear 1603 (e.g., a tongue of the footwear). Additionally or alternatively, the device assembly 1616 may be engaged directly to a portion 1604 of the footwear 1603 configured to receive the device assembly. In some aspects of the present disclosure, the device assembly 16 may be placed within a receptacle 1622 configured to be engaged with or embedded within the article of footwear 1603. As will be appreciated, the device assembly 1616 may also be placed (or secured) to any other desired location on footwear 1603.

As discussed above, a carrier can be incorporated into apparel such as shirts, pants and shoes. Other items of apparel are also possible. Other items are also possible such as bags, totes, bands, accessories or any other kind of article worn by a person. For example, a USB device and/or device assembly may be embedded within or attached to a portion of an article of footwear (e.g., a tongue of the footwear, etc). Additionally or alternatively, as illustrated in the example embodiments depicted in FIGS. 16C-E, a USB device and/or device assembly as described herein may be attached to various types of athletic equipment (e.g., FIGS. 16C and 16D) and/or other articles or items (e.g., FIG. 16E).

As depicted in the example embodiment depicted in FIG. 16C, a USB device 1650 can be attached to (and/or engaged with) a piece of athletic equipment. There are a variety of ways in which the USB device may be attached to and/or engaged with a piece of athletic equipment, such as a skateboard or golf club. For example, as illustrated by element 1658 in FIG. 16C, a securing element may be configured to receive the USB connector of USB device 1650. The securing element 1658 may be further configured to be attached to a portion of the piece of athletic equipment (e.g., skateboard 1645). For example, the securing element depicted in FIG. 16C may be secured to a portion of the skateboard 1645 using a fastener. Additionally or alternatively, the USB device 1650 may be directly engaged with and/or connected to the piece of athletic equipment. In some aspects of the present disclosure, a portion or segment of the athletic equipment may be configured to receive a communication connector of USB device 1650. For example, as illustrated by FIG. 16D, a first portion of golf club 1660 (e.g., golf club head 1661) may include a securing element (or aperture) configured to receive a communication connector of USB device 1650. As another example, a second portion of golf club 1660 (e.g., golf club handle 1662) may include a securing element (or aperture) configured to receive a communication connector of USB device 1650. Additionally or alternatively, securing element 1658 (configured to receive a communication connector of USB device 1650) may be attached to or operatively engaged with the handle 1662 of athletic equipment 1660.

In some aspects of the present disclosure, the USB device (and/or device assembly) may communicate with one or more sensors engaged with and/or operatively connected to a piece of athletic equipment. The USB device may be configured to receive sensor data collected by the one or more sensors associated with the piece of athletic equipment. In some arrangements, the USB device may measure performance characteristics (or other parameters) based on the sensor data. For example, with respect to a golf club, a USB device may be engaged at the handle/grip of the golf club and may be in communication with one or more sensors connected to various locations of the golf club. In this example, the USB device may calculate one or more performance characteristics or parameters (e.g., swing velocity) based on the data collected by said sensors. Additionally, as depicted in the example embodiment depicted in FIG. 16E, the USB device 1670 can also be attached to various other types of apparel or items, such as bracelets, rings, armbands, necklaces, and the like. For example, as shown in FIG. 16E, USB device assembly 1670 may be attached to an armband 1671, or placed within a pocket of armband 1671. As another example, USB device 1675 may be engaged with an aperture of wristband 1672 that is configured to receive a communication connector of USB device 175, such that the USB device 1675 is secured to a user's wrist when the wristband 1672 is worn. As yet another example, USB device 1676 may be engaged with an aperture of ring 1673 such that the USB device 1676 is secured to a user's finger when the ring 1673 is worn. As discussed above, such USB devices (and./or device assemblies) may be configured to monitor various aspects of user movement during an athletic performance, and sensors within and/or operatively connected to said USB devices may be configured to record performance data based on the one or more physical movements of a user during the athletic performance.

Data Transmission Systems:

The USB device (and/or device assembly) as described herein may include and/or operatively connect with one or more data transmission/reception elements capable of electronic communication and data transfer with one or more remote devices (e.g., communication and data transfer with a transmission/reception element provided with a remote device). Electronic communications in any form, using any desired data transfer forms, formats, and/or protocols, may be used without departing from the present disclosure. As examples, the data transmission system 937 described above with respect to FIG. 9A may include one or more data transmission/reception elements (not shown) configured to communicate with other transmission/reception elements (e.g., transmission/reception elements associated with and/ or connected to other computing devices) in wired or wireless manners without departing from the present disclosure. As some more specific examples, the data transmission/reception elements may communicate with one another via radio transmissions, cellular telephone transmissions, infrared radiation transmissions, RFID transmissions, or the like. Also, if desired, the data transmission/reception systems 937 of the USB device may be capable of both sending data to and receiving data from a remote system (e.g., a remote computing device), to thereby enable two way communications between the USB device and the remote system without departing from the present disclosure (e.g., to allow data input to the USB device 16 and/or its various components, if necessary or desired, for example reasons to be explained in more detail below, etc.).

As discussed above, FIG. 9A includes an exemplary schematic diagram of a USB device including data transmission/reception capabilities that may be used in accordance with at least some examples of this disclosure. While the example structures of FIG. 9A illustrate the data transmission/reception system 937 as integrated into the USB device structure, those skilled in the art will appreciate (as described in various examples below) that a separate component may be included as part of the USB device structure or other structure for data transmission/reception purposes and/or that the data transmission/reception system 937 need not be entirely contained in the housing of the USB device in all examples of the present disclosure. Rather, if desired, various components or elements of the data transmission/reception system 937 may be separate from one another and/or separately engaged with other devices in a variety of different manners without departing from the present disclosure.

As discussed above, in other aspects of the present disclosure, a first USB device may be in communication with and/or operatively connected to a second USB device and/or an electronic device (e.g., sensor 12) provided as a component of the performance monitoring system 10 to sense or provide data or information relating to a wide variety of different types of parameters, such as physical and/or physiological data associated with use of the second USB device (and/or sensor 12); or a performance of the user, such as pedometer type speed and/or distance information, other speed and/or distance data sensor information, temperature, altitude, barometric pressure, humidity, GPS data, accelerometer output or data, heart rate, pulse rate, blood pressure, body temperature, EKG data, EEG data, etc., and this data may be stored in memory and/or made available, for example, for transmission by the transmission/reception system 937 to some another computing device and/or a remote location or system. In some aspects of the present disclosure, USB device 16 may include one or more electronic devices (e.g., sensors) to monitor and/or record the various types of performance parameters, as described above and herein.

For example, a first USB device attached to a user may be configured to obtain location data via a GPS receiver, while a second USB device attached to the user may be configured to obtain speed and distance data via an accelerometer. In this example, the first USB device may communicate with and/or operatively connect to the second USB device. In some aspects of the present disclosure, the first USB device or the second USB device may include a data transmission/reception element for transmitting data obtained by the USB devices. In other aspects of the present disclosure both the first and second USB devices may include data transmission/reception elements. As another example, a USB device may communicate with and/or operatively connect to one or more electronic devices (e.g., sensors) and may include a data transmission/reception element for transmitting data obtained by the USB device and/or the electronic device. For instance, a first USB device (configured to obtain location data via a GPS receiver) may communicate with an electronic device (e.g., a sensor) configured to obtain body temperature data via a temperature sensor, and the USB device may be further configured to transmit to a remote system information collected by the USB device as well as information collected by the temperature sensor. In other aspects of the present disclosure, an electronic device in communication with the USB device may include (and/or be operatively connected to) a data transmission/reception system, such that the electronic device (e.g., sensor) may transmit sensor data to the USB device, and/or to a remote system or other suitable computing device.

Figure 17:
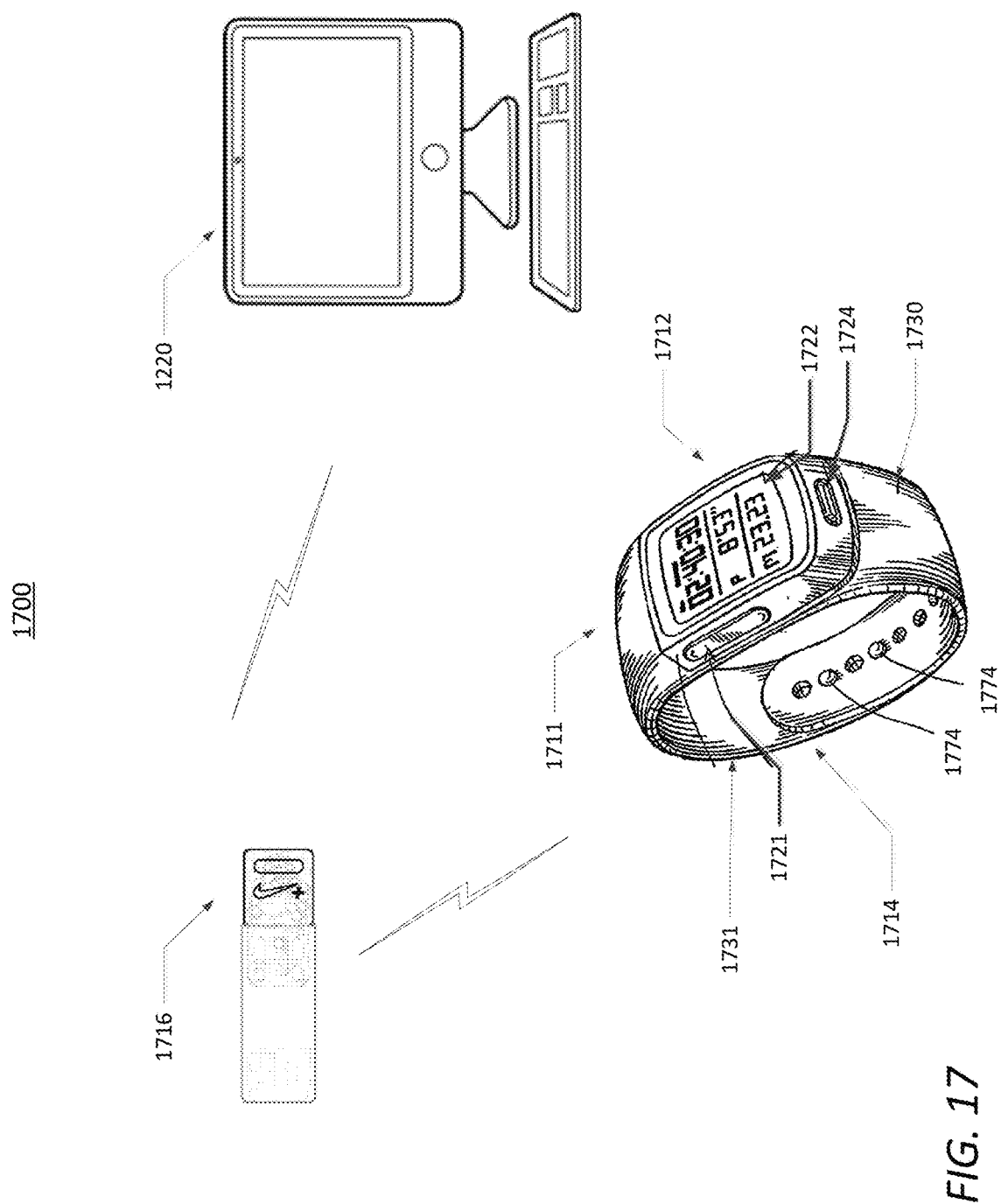
FIG. 17 is a perspective view of a performance monitoring system including a USB-type device and other computing devices according to one or more aspects of the present disclosure.

As described above with respect to FIG. 1, aspects of the present disclosure relate to systems and methods that may be utilized across a plurality of networks. In this regard, certain embodiments may be configured to adapt to dynamic network environments. FIG. 17 illustrates an example of a performance monitoring system 1700 in accordance with example embodiments. Example system 1700 includes a USB device assembly 1716, a remote computing device 1720, and portable computing device 1711 and may also include one or more interconnected networks. In some aspects of the present disclosure, portable computing device (1711 may be programmed and adapted to perform various functions in conjunction with USB device 1716 in accordance with examples of the present disclosure. In this illustrated example, the portable computing device 1711 includes the data transmitter/receiver element (not shown) as well as display device 1712 (including a video/alphanumeric display device 1722 and audio speaker 1724) and user input device 1721. The remote device 1711 further includes a band member 1214, e.g., for attachment to a user's clothing, body, or equipment. Of course, any desired type of system may be provided for attaching this remote device 1711 to another object, if desired, including bands of different types (e.g., various types of watch-type bands), chains or other neck engaging devices, clips, clamps, clasps, mechanical fasteners, and the like. As further shown in FIG. 17, the remote device 1711 may include a wristband configured to be worn by a user. The wristband may include a first end 1730 and a second end 1731. The first end 1730 may include one or more holes to accommodate a plurality of posts located on the second end 1731 of the strap. By engaging the posts 1774 with the one or more holes, the user may fasten the wristband to a wrist of a user. With the use of a pair of posts 7174, the wristband allows for a secure connection and greater flexibility in connection providing for a greater adjustment to accommodate for a range of wrist sizes.

The video/alphanumeric display device 1722 may be configured to display information, e.g., to the wearer of the USB device or to a third party, wherein the displayed information may be based, at least in part and in some instances, on the data transmitted by the USB device 1716. In some aspects of the present disclosure, the remote device may comprise a computing device operated by a third-party. As illustrated in FIG. 17, in some example embodiments, the remote device 1711 may comprise a portable electronic device worn by the wearer of the USB device assembly 1716. Additionally or alternatively, if desired, the remote device 1711 may include a user input system, for receiving user input, e.g., to enter or adjust settings, to control the functions or settings of the remote device 1711 or various components thereof, and/or to enter settings or control the functions of the USB device 1216 or the various components thereof. In some embodiments, the user input system may be configured to control a plurality of USB device. Any desired type of input system may be provided without departing from the present disclosure, including, for example, a keyboard input, a stylus type input, a voice input, a button type input, a soft keyboard, etc.

If desired, user input and/or other data or information accepted and/or generated by the remote device 1711 may be transmitted back to the USB device 1716, e.g., via a data transmission/reception element (not shown). Alternatively or additionally, if desired, user input or other data or information generated by the remote device 1711 may be sent to the USB device 1716 and/or to one or more other remote systems (e.g., remote system 1720) via an input/output system (e.g., a data transmission line, a wireless transmission system, an internet connection, etc.). The remote system 1720 may take on any desired form without departing from the present disclosure, such as a computer or computing system, a remote display device, another data transmission system, or the like. If desired, communication directly between the remote system 1720 and the USB device 1716 may be enabled (without the need to pass through the intermediate remote device 1711). Connections between the remote system 1720, remote device 1711, and/or the USB device 1716 may take on any desired form, as described above with respect to FIG. 1, such as wired or wireless connections, and the data may be transferred in any desired form or format without departing from the present disclosure.

Device Activation/Interaction Systems:

If desired, systems and methods according to this example aspect of the present disclosure (as well as the various aspects of the present disclosure described above) further may include a USB device activation system for activating a USB device as described herein. This activation system, in some examples, may constitute an ON/OFF switch or button. If desired, the activation system may be located at a remote or not easily accessible position in the USB device, e.g., within the interior of the surface of the housing of the USB device, such that activation tool of some sort may be required to activate the USB device. In some aspects of the present disclosure, the activation system may include a button (e.g., button 33) on the housing 20 of the USB device itself or an activation system activated by a tool as described above through an opening defined in the housing of the USB device.

In some aspects of the present disclosure, the USB device activation system may sense whether a first USB device is engaged with a receiver member (and/or a piece of athletic equipment, an article of footwear, an article of apparel, etc.) and activates the USB device or at least a first function of the USB device when the USB device is determined to be engaged with the receiver member (and/or a piece of athletic equipment, an article of footwear, an article of apparel, etc.). If desired, at least a first portion of the activation system may be included with and/or as part of the USB device, and a second portion of the activation system may be included with and/or as part of the receiver member. In other aspects of the present disclosure, at least a first portion of the activation system may be included with and/or as part of the USB device and a second portion of the activation system may be included with and/or as part of an article of clothing, an article of footwear, a piece of athletic equipment, and the like. In other examples, if desired, the USB device may include both the source and the sensor, but changes in the sensed magnetic characteristics or an interrupted light beam may be sensed when the USB device is engaged with the receiver member (e.g., closure member, second USB device, etc.).

As noted above, in some aspects of the present disclosure, one or more functions of the USB device may be activated or enabled by actuating a button on the USB device. In at least some other aspects of the present disclosure, the USB device, or at least some functions of the USB device, may be initiated or enabled automatically, for example, whenever the USB device is engaged at a receiver member (and/or a piece of athletic equipment, an article of footwear, an article of apparel, etc.) and/or whenever the USB device is detected as being engaged at a receiver member (and/or a piece of athletic equipment, an article of footwear, etc.). Determination as to whether the USB device is engaged with the receiver member (and/or a piece of athletic equipment, an article of footwear, etc.) may take place in any suitable or desired manner without departing from the present disclosure. For example, the activation system may include a magnetic sensor system, a piezoelectric system, an accelerometer, a light sensor, or the like that produces an output when the USB device is included at and/or engaged with the receiver member (and/or a piece of athletic equipment, an article of footwear, etc.). In some examples, when the activation system includes a magnetic sensor, such as a Hall sensor system, a first portion of the magnetic sensor system (e.g., a magnet, a magnetic sensor, etc.) may be included with the receiver member (and/or piece of athletic equipment, article of footwear, etc.), and a second portion of the magnetic sensor system (e.g., a magnetic sensor, a magnet, etc.) may be included with the USB device.

As noted above, activation and/or authentication systems in accordance with at least some examples of the present disclosure may include a wide variety of different structures, at a wide variety of different locations, including the various structures and locations described above. As still further examples, the activation and/or authentication systems may include one or more members of a first USB of the first USB device (e.g., USB connector 23) that extends into one or more openings, recesses, grooves, and/or discontinuities provided in a housing structure (e.g., the housing of the receiver member, the housing of a second USB device, etc.). In at least some instances, use of the activation and/or authentication systems will result in making an electrical connection, e.g., between a first electrical conductor provided with the USB device and a second electrical conductor provided with the housing of the receiver member and/or the housing of the second USB device.

In at least some examples of the present disclosure, the USB device, or at least some functions of the USB device, may be initiated or enabled automatically, for example, whenever the USB device is engaged with a receiver member and/or a second USB device. In accordance with other aspects of the present disclosure, however, activation of the USB device and/or various functions of the USB device may be somewhat more selective. In some aspects of the present disclosure, if the USB device is engaged with the receiver member (and/or piece of athletic equipment, article of apparel, etc.) in a manner other than in a first orientation (e.g., other than in a predetermined activation orientation), the USB device may be shut off, deactivated, disabled, not turned on, and/or not activated and/or various functions of the USB device may be shut off, deactivated, disabled, not turned on, and/or not activated.

These example features of the present disclosure may be used to easily switch the USB device and/or various functions of the USB device on and off. As some more specific examples, when the USB device is engaged with a receiver member (and/or a second USB device, etc.) in the first orientation, this may turn the USB device on and/or activate various functions of the USB device. Removing the USB device from the receiver member (and/or a second USB device, etc.), flipping it over, rotating it, and/or the like, and then re-engaging it with the USB device securing element may be detected, e.g., by a magnetic sensor or other detector systems as described above, and these changes will place the USB device at an orientation other than the predetermined activation orientation. In response to these orientation changes and/or in response to the USB device being engaged with a receiver member (e.g., a second USB device, closure member, etc.) in an orientation other than the predetermined activation orientation), the USB device may be shut off and/or various functions of the USB device may be shut off, disabled, etc. This example feature may be used to extend battery life. In at least some aspects of the present disclosure, if an item with which the USB device has been engaged (e.g., a piece of athletic equipment) and the USB device do not each include the corresponding parts of the activation system and/or do not otherwise induce an expected interaction and/or change in detected interaction, the USB device may not be activated and/or may be disabled and/or various functions of the USB device will not be activated and/or will be disabled.

The interaction between the USB device and the USB device activation system may be used for other purposes as well. For example, in accordance with at least some example aspects of the present disclosure, features relating to the interaction between the USB device and the activation systems may be used to provide information to a data processing system associated with the USB device (e.g., on board and/or in communication with the USB device), and/or to provide information as to what data processing algorithm should be used, for example, to process data sensed, collected, and/or generated by the sensor(s) included with the USB device or operatively connected to the USB device (e.g., included in a receiver member, an article of footwear, a piece of athletic equipment, etc.).

Various ways of changing or controlling the interaction between the USB device and the receiver member (and/or piece of athletic equipment, article of apparel, etc.) may be used without departing from the scope of the present disclosure. For example, if the USB device activation system includes a magnetic based sensor system, aspects of the interaction between the USB device and the USB device activation system may be changed or controlled, for example, by changing the orientation, position, location, magnetic field orientation, and/or pole orientation of one or more magnets with respect to the magnetic sensor element(s); by changing the strength of one or more of the magnets; etc. Different orientations, positions, locations, magnetic field orientations, magnetic pole orientations, strengths, composite magnetic field strengths, composite magnetic field orientations, and the like may be sensed by systems and methods in accordance with examples of the present disclosure and used as information to control and/or select the data processing algorithm used when the data is collected. Of course, light sources and light sensors (or other detection systems) may be used and various different characteristics regarding the detected light (or other parameter) may be used to control and/or select a data processing algorithm for use. Combinations of various different sensors and/or sensed parameters also may be used without departing from the scope of the present disclosure.

As even more specific examples, different orientations, positions, locations, magnetic field orientations, magnetic pole orientations, magnetic strengths, composite magnetic field strengths, composite magnetic field orientations, light positions, light wavelength, transmitted/reflected lights and/or patterns, light intensity, and the like may be sensed by systems and methods in accordance with examples of the present disclosure discussed above and used to indicate, for example, a type of receiver member (and/or type of sensor device therein) with which the USB device is engaged, a type of clothing or equipment with which a USB device is operatively engaged, a mounting location on an article of clothing or piece of athletic equipment with which the USB device has been engaged, etc.

The USB device may be controlled (e.g., by a processor 39) to initiate a specific type of data processing algorithm and/or to sense specific types of data or information associated with the indicated type of clothing or equipment or location information. Additionally or alternatively, information obtained by the USB device and activation system may be used, at least in part, in selecting a data processing algorithm for use by the USB device (e.g., to determine the type of physical and/or physiological parameters to measure, to determine the type of information data provided for display, to determine characteristics of the data collection or display, etc.) and/or in selecting various components of the system to activate and/or utilize.

As additional more specific examples, an individual article of clothing or piece of athletic equipment may be attached to or operatively engaged with plural USB devices (e.g., one high on a leg, one low on a leg, etc.). Different magnet arrangements or conditions (or light sources or other USB device activation system elements or conditions) may be associated with each of the USB devices so as to enable the sensor system (or performance monitoring system) to determine the location on the article of clothing or piece of athletic equipment where the USB devices are engaged. Optionally, each USB device engaged with the article of clothing or piece of athletic equipment may have its own independent, associated magnets or other USB device activation systems, or alternatively, if desired, portions of one USB device activation system may be shared by more than one USB device (e.g., by varying distance, direction, orientation, intensity, etc. at the various locations at which the USB device may be attached, etc.). Different sensors may be activated by the USB device (and/or within a receiver member, other USB device(s), article of equipment, etc.), different data algorithms may be run, and/or different information may be presented to the user (or third-parties) depending on which USB device engaged with the article of clothing or piece of athletic equipment is sensed as being utilized by the user.

Additional features relating to this aspect of the present disclosure relate to physical and/or physiological parameter sensing systems to sense one or more characteristics of a user performance. Still additional features relating to this aspect of the present disclosure relate to methods for activating USB devices using the various systems and methods described above.

Figures 18A, 18B:
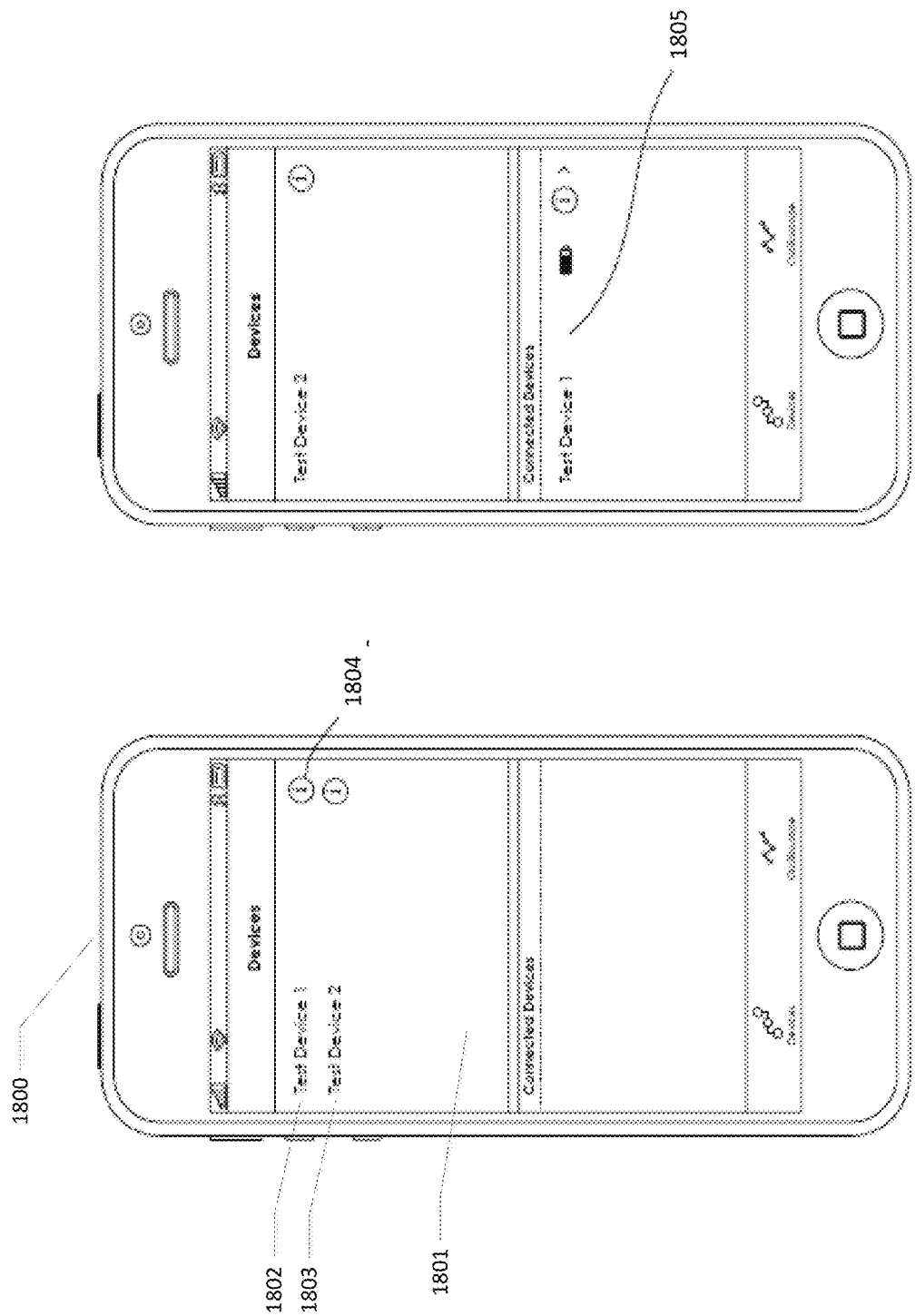
FIGS. 18A-B illustrate example user interface screens in accordance with one or more aspects of the disclosure.

User Interface Systems & Software Applications:

It is understood that the various embodiments of the device disclosed herein may utilize user interface features. FIG. 18A illustrates an example of an athletic information collection and display device 1800 that may be employed to collect and/or display performance data according to various implementations of the present disclosure. In some aspects of the present disclosure, device 1300 may include one or more of the same operational features as portable device 112 as described above with respect to FIG. 1. As will be discussed in more detail below, the athletic information collection and display device 1800 may display a user interface and may both collect and display performance data. The athletic information collection and display device 1800 may be implemented using any suitable variation of computing devices. In some embodiments, information collection and display device 1800 may be implemented using a desktop, laptop, personal computer, mobile computing device, and the like.

As shown in the example embodiment depicted in FIG. 18A, the athletic information collection and display device 1800 includes an interface for receiving data from one or more devices (e.g., USB device 16). The interface may be implemented using, e.g., electrical components, software components (such as application program interfaces (APIs)), or some combination thereof. The athletic information collection and display device 1800 may include an athletic data collection module. With various examples of the present disclosure, the athletic data collection module may detect when USB device 16 (and/or other electronic devices or components storing one or more performance data sets) is connected, wirelessly or otherwise, to the athletic information collection and display device 1800 through the interface, establish a communication session with the USB device 16 or other electronic devices to retrieve performance data.

As will be appreciated, in some aspects of the present disclosure, the device 1800 utilized by the user to view the performance data may be equipped with a touch-sensitive display screen configured to recognize one or more physical gestures performed by the user as user input. For example, the device may recognize an upward finger swipe performed by the user on the touch-sensitive display screen as user input corresponding to an upward scroll. Accordingly, upon recognizing this user gesture, the device may scroll the interface being displayed on the device display upward. As another example, the device may recognize a single tap on the display screen as a user input selection. The user may also rotate, swipe, tap, or pinch the device display as a means of inputting data or selecting options and/or interface elements within the interface. Any suitable method of inputting data or selecting options within the interface display may be implemented without departing from the present scope of the disclosure, including, for example, a keyboard input, a stylus type input, a voice input, a button type input, a soft keyboard, etc.

As previously noted, the athletic information collection and display device 1800 typically may generate sets of performance data from information measured by one or more devices, such as USB device 16 or other electronic devices (e.g., sensors). With some embodiments of the present disclosure, however, the athletic information collection and display device 1800 may instead store the raw information provided by the USB device 16. With these embodiments, the athletic data collection module may retrieve the raw information from the USB device 16 or other portable electronic device, and then generate athletic data sets from the raw information itself. As will be explained in more detail below, in some aspects of the present disclosure, the data collection module may be configured to stream (in real-time) raw information recorded by USB device 16, and display said data in the user interface.

The athletic data collection module may be implemented by, for example, software instructions executed by a computing device, such device 1800 or any other suitable computing device. With some examples of the present disclosure, the athletic data collection module may be implemented by a conventional software tool, such as a browser or other desktop application. Alternately, athletic data collection module may be implemented by a purpose-specific software tool, mobile application, or by a conventional software tool enhanced to perform athletic data collection functions. For example, the athletic data collection module may be implemented by a software tool that incorporates a conventional browser to perform a variety of functions.

Additionally, data collected using systems and methods in accordance with examples of the present disclosure may be uploaded, including sensor data relating to an athletic performance, from the USB device 16 at which it is initially collected and stored on a separate computing device, e.g., such as a personal computer, laptop, palmtop, cellular telephone, personal digital assistant, etc. Additionally or alternatively, the computing device further may transfer the data to a networked site (e.g., a web-based application), optionally for use by a user, or in a community setting (where performance data from several users is accepted, shared, stored, etc.). As a more specific example, systems and methods in accordance with at least some examples of the present disclosure may be used in conjunction with hardware and software like that used in the systems and methods commercially available from NIKE, Inc. of Beaverton, Oreg. under the trademark NIKE+.

In some aspects of the present disclosure, the USB device 16 may include additional capability for uploading sensed activity or performance data to other remote locations such as locally on a personal computer, mobile device, or a remote website for further display, review and monitoring. To this end, it is understood that the controller 21 of the USB device 16 has an appropriate user interface wherein a user can download appropriate software via a computer from a remote location. The USB device 16 may be removed from a receiver member and/or carrier, and then plugged into the standard USB hub/port on a computer (see FIG. 9). Once the appropriate software is installed, the application may commence with USB device 16 still being plugged into the computer. In other aspects of the present disclosure, a user may download the appropriate software from a remote networking site prior to utilizing the USB device 16.

As described above, during a performance monitoring session, USB device 16 may record and/or transmit performance data to a computing device (e.g., mobile device) or an athletic data collection module associated with a computing device. The athletic data collection module of the computing device (e.g., athletic information collection and display device 1800) may display the performance data via the user interface. Additionally or alternatively, once the athletic data collection module has collected the processed signals (e.g., performance data) provided by the USB device 16, the athletic data collection module may transmit the performance data to an athletic information collection and display device 1800.

The USB device 16 may communicate with the athletic information collection and display device 1800 through a conventional network, such as the Internet. Additionally or alternatively, the USB device 16 may communicate with the athletic information collection and display device 1800 using any suitable type of electronic communication, such as Bluetooth low energy (BLE) communications. In some aspects of the present disclosure, the athletic information collection and display device 1800 may transmit recorded performance data to other computing devices. Any type of desired hardware or software combination may be used to allow the athletic data collection module of athletic information collection and display device 1800 to send collected performance data to another computing device.

FIGS. 18A-B further depict exemplary display screens that may be provided on an interface (e.g., interface 1801) of athletic information collection and display device 1800. In the example illustrated in FIG. 18A, display screen 1801 indicates that the athletic information collection and computing device (e.g., device 1300) has detected (and/or previously recognized) two USB-type monitoring devices as described herein (i.e., Test Devices 1 and 2). The interface may display indicia (e.g., icon, text, graphic) identifying each of the various devices detected (and/or previously recognized) by device 1800. For example, referring to FIG. 18A, the interface displays indicia 1802 (i.e., "Test Device 1") to indicate a first recognized USB device, and indicia 1803 (i.e., "Test Device 2") to indicate a second recognized USB device. In some embodiments, the user may access a device configuration interface and/or be provided with an option to select the particular indicia to be associated with each recognized device. Additionally or alternatively, a user may revise the title or name associated with each detected USB device.

In some embodiments, a portion of the interface may display an icon (or other suitable interface element), that when selected by a user, may cause the device 1800 to attempt to locate and/or establish a communication relationship with a recognized USB device. For example, referring to FIG. 18A, if a user selects icon 1804, the computing device may attempt to establish a communication relationship with Test Device 1. In some aspects of the present disclosure, an indicator system of Test Device 1 (e.g., indicator system 412) may notify the user that a computing device is attempting to establish a communication relationship with the Test Device 1. For example, one or more lighting elements of the indicator system for Test Device 1 may be illuminated to notify a user that a computing device is attempting to establish a communication relationship. After Test Device 1 has been located by device 1800, the interface may display a message or notification prompting the user to confirm the communication relationship established with Test Device 1. As illustrated in display screen 1805 of FIG. 18B, in some example embodiments, the interface may indicate that a communication relationship has been established with a particular USB device by displaying the indicia associated with that device in a portion of the interface associated with connected devices. In other aspects of the present disclosure, the indicator system of Test Device 1 may notify the user that a communication relationship has been established with another device and/or closure member. For example, one or more lighting elements of the indicator system for Test Device 1 may be illuminated to notify a user that a device (and/or a closure member) has established a communication relationship with Test Device 1.

Figures 19A, 19B:
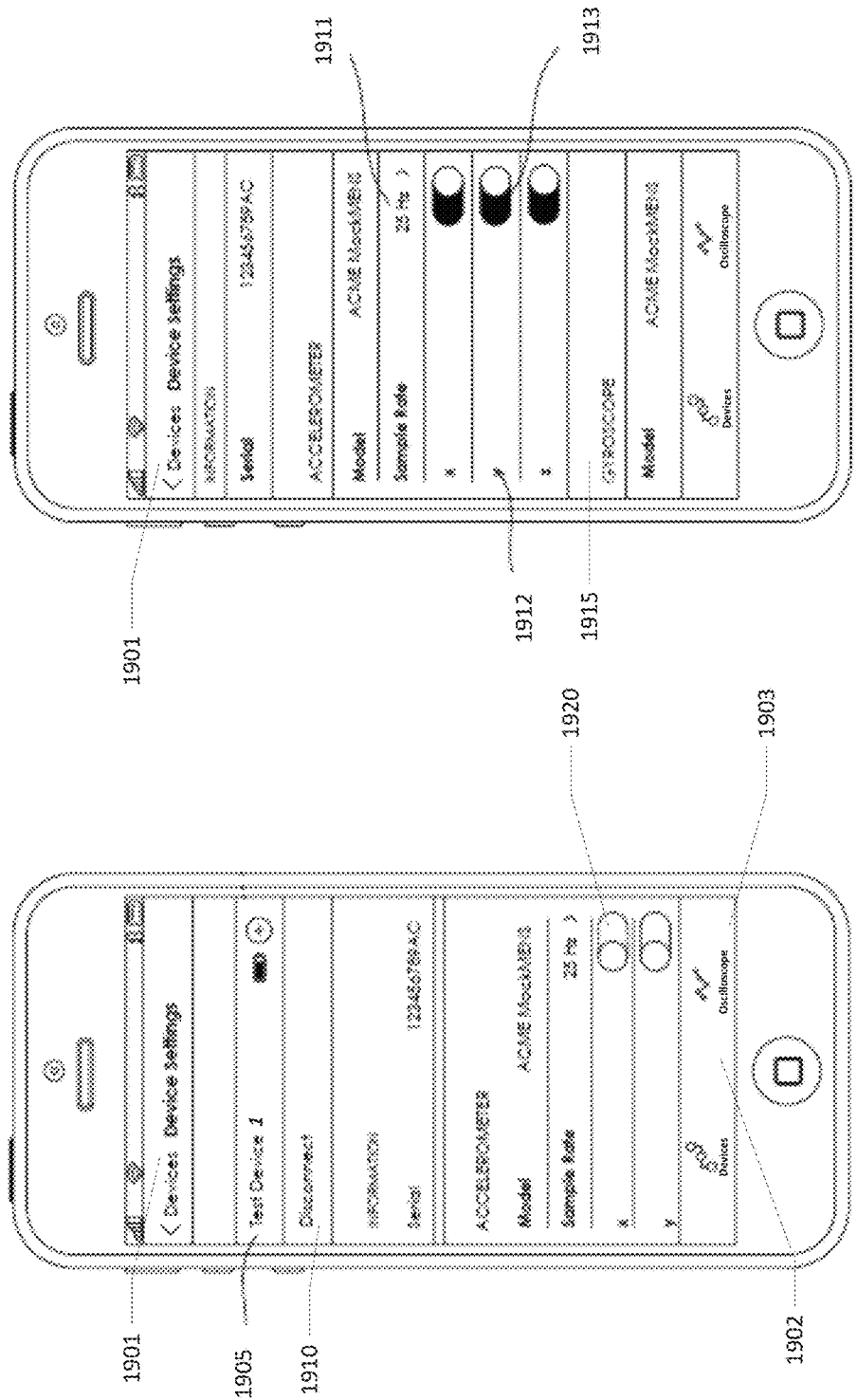
FIGS. 19A-B illustrate example user interface screens in accordance with one or more aspects of the disclosure.

As shown in the example embodiment depicted in FIGS. 19A-B, the interface may provide the user with a device configuration display screen wherein the user may modify or identify particular setting for a USB device recognized by and/or connected with device 1800. A user may access device settings for a USB device by selecting the indicia associated with the desired USB device via an input system for device 1800 (e.g., touch-screen display). For example, in response to a user selecting indicia 1802 in FIG. 18A, the device 1800 may display a device configuration interface screen as depicted by display screen 1901 in FIG. 19A. As further illustrated in the example embodiment depicted in FIG. 19A, a user may end a communication relationship with a USB device by selecting the "Disconnect" interface element 1910 in device configuration interface screen 1901. The device configuration interface screen may provide additional information associated with a particular device, such as a unique identifier for the device (e.g., serial number), an identification of the various sensors or other electronic components associated with the device, and other types of information. As will be described in more detail below, a portion 1902 of device configuration interface screen 1901 may provide the user with access to additional interface screens. For example, as will be described in further detail below, the user may access an oscilloscope interface screen by selecting icon 1903.

As shown in the example embodiment depicted in FIGS. 19A-B, the device configuration interface 1901 may identify the various sensors associated with the selected USB device (i.e., Test Device 1). As illustrated in FIG. 19A, Test Device 1 includes (and/or is operatively connected to) at least a first accelerometer. Interface 1901 may identify the selected USB device in a portion 1905 of the display screen. The device configuration interface screen may provide various data and information associated the first accelerometer, such as the model number, a current sampling rate, and other information with departing from the scope of the present disclosure. In other aspects of the present disclosure, a user may configure various aspects of a detected sensor (e.g., accelerometer) via the device configuration interface screen. For example, as illustrated by FIG. 19B, a user may modify the sampling rate for a sensor by selecting a portion 1911 of the device configuration interface screen 1901. In some embodiments, a user may identify the various sensors (and/or components thereof) included in and/or operatively connected to Test Device 1 for which the user wishes to collect performance data. For example, a user may enable a particular component (e.g., x-axis) of the accelerometer by selecting a portion of device configuration interface screen. In this example, a user may enable the x-axis of the accelerometer by selecting (e.g., tapping, swiping right) a portion 1920 of the device configuration interface screen 1901. Additionally or alternatively, a user may disable a component (i.e., y-axis) of the accelerometer shown in portion 1912 of the interface screen by selecting (e.g., tapping, swiping left) portion 1913 of the device configuration interface screen 1901. As noted above, a user may utilize an input system to access additional portions of device configuration interface screen 1901. As shown in the example embodiment depicted in FIG. 19B, the configuration interface screen 1901 may display information and device settings for additional sensors and/or electronic components included in (and/or operatively connected to) Test Device 1, such as the gyroscope displayed in portion 1915 of interface 1901.

In some aspects of the present disclosure, a user may create and/or save customized configuration settings for various devices (e.g., sensors) via the device configuration interface screen. In some embodiments, the user may associate a particular saved device configuration setting with different types of athletic performances and/or activities. For example, when utilizing the USB device to measure performance data associated with basketball-related activities (e.g., jumping, shooting, dunking, running, etc.) the user may identify a first device configuration setting for a sensor of the USB device. Alternatively, when utilizing the USB device to measure performance data associated with soccer-related activities (e.g., sprinting, dribbling, passing, etc.) the user may identify a second device configuration setting for the sensor of the USB device. Any number of predetermine (or stored) device configurations may be associated with a particular sensor without departing from the scope of the present disclosure.

FIG. 20A illustrates an example user interface that may be displayed to a user as a result of initiating icon 1903 of interface 1901 as described above with respect to FIG. 19A. In this illustrated example, interface display 2001 may be presented to a user attempting to initiate a performance monitoring session via Test Device 1 (e.g., USB device selected by user). Interface display 2001 may be configured to display performance data collected by Test Device 1 during (or after) the performance monitoring session. Interface display 1701 may include a plurality of interface elements that allow the user to control the monitoring and/or recording of performance data. For example, by selecting the "record" icon 2003, a user may begin recording on a device (e.g., device 1800) performance data collected or sensed by one or more sensors included in and/or operatively connected to Test Device 1. In this example, the performance data recorded by device 1800 may be stored in a memory unit or other suitable storage. As another example, by selecting the "play" icon 2004, a user may playback the performance data recorded by device 1800 with respect to the one or more sensors included in and/or operatively connected to Test Device 1.

As yet another example, referring to FIG. 20B, by selecting the "stop" icon 2005, a user may stop the device (e.g., device 1800) from recording performance data collected by one or more sensors included in and/or operatively connected to Test Device 1. In some embodiments, after selecting stop icon 2005, the device (e.g., device 1800) may be configured to store the recorded performance data in a data file. In some of these embodiments, the device 1800 may associate or assign a time stamp with the associated data file. In other embodiments, the device 1800 may associate other device information, as described above, with the associated data file. In some aspects of the present disclosure, a user may pause the recording of performance data by selecting icon 2005. In such arrangements, the user may resume the recording of performance data by selecting icon 2004. In some embodiments, after the recording of performance data has been paused and then subsequently resumed, the previously recorded performance data and current data being recorded by device 1800 may be included within the same data file. In other embodiments, upon resuming the recording of performance data, the performance data may be store in a new data file the performance data recorded prior to the recording being paused, and subsequent recorded performance data may be stored in a new data file.

As illustrated in the example embodiment depicted in FIG. 20A, a portion 2010 (e.g., oscilloscope display 2010) of the interface screen 2001 may display a visual depiction of the performance data collected by a USB device (e.g., Test Device 1) in accordance with the systems and methods described herein. In particular, oscilloscope display 2010 may display a visual depiction of the raw data collected by the one or more sensors included in and/or operatively connected to Test Device 1. As described above with reference to FIG. 19B, the performance data may be obtained/recorded using a specified sampling rate. Additionally or alternatively, performance data may be obtained/recorded during a predetermined sampling time period. As illustrated in FIGS. 20A-B, in some example embodiments, device 1800 may provide in interface display 2010 a plot (and/or one or more traces) of collected performance data. As will be discussed in more detail below, each trace in the interface display may correspond to a sensor and/or sensor component (e.g., sensor axis) that is monitoring and recording athletic performance during a performance monitoring session.

As illustrated in the example embodiment depicted in FIG. 21A, a portion 2009 (e.g., "Show Key" icon 2009) in interface 2001 may provide a user with access to a user interface configured to modify or select the performance data displayed in oscilloscope display 2010. FIG. 21B illustrates an example user interface that may be displayed to a user as a result of initiating icon 2009 as described above with respect to FIG. 21A. In this illustrated example, interface display 2110 may be presented to a user attempting to modify or select the particular performance data displayed in oscilloscope display 2010. As shown in FIG. 21B, interface display 2110 may provide a list of available sensors and/or sensor components (e.g., sensor axis) configured to collect performance data for Test Device 1. In some embodiments, by selecting a specified portion of interface display 2110, a user may determine which sensor (or sensor component) data will be displayed in oscilloscope display 2010. For example, as illustrated in FIG. 21B, the sensor data for sensor components Accel. X, Accel. Y, Accel. Z, and Gyro.X are currently configured to be displayed in oscilloscope display 2010, while sensor components Gyro.Y and Gyro.Z are configured to be hidden. A user may hide the performance data collected by Accel. X from being displayed in oscilloscope display 2010 by selecting icon 2113. In this example, a portion of interface display 2110 may be updated to reflect that the Accel. X data is now hidden (e.g., see element 2114).

In other aspects of the present disclosure, the plurality of traces displayed in oscilloscope display 2010 may be color-coded to associate a trace with its corresponding sensor (or sensor component). Interface display 2110 may include a color-coded key (or legend) indicating which colors have been assigned to each sensor (or sensor component) trace for oscilloscope display 2010. For example, as depicted by element 2115 in FIG. 21B, the sensor data collected by Accel.X will be represented as a Red trace in oscilloscope display 2010. As another example, as depicted by element 2116 in FIG. 21B, the sensor data collected by Accel.Y will be represented as a Blue trace in oscilloscope display 2010. As will be appreciated, any suitable method of distinguishing sensors and corresponding sensor data in display 2010 may be employed by device 1800 with departing from the scope of the present disclosure.

With some implementations of the present disclosure, the USB device (e.g., Test Device 1) may be configured to automatically forward recorded performance data to a computing device (e.g., athletic information collection and display device 1800). For example, the Test Device 1 may attempt to forward collected performance data to the athletic information collection and display device 1300 in real time and/or immediately after collection, at a prescheduled interval, upon the detection of a network connection to the device 1800, or some combination thereof. Alternately or additionally, the athletic data collection module may prompt a user when performance data collected by Test Device 1 is available. In other aspects of the present disclosure, a user may specify, via a user interface 1801, when collected performance data should transmitted from Test Device 1 to device 1800. In other aspects of the present disclosure, athletic information collection and display device 1800 may be configured to automatically forward recorded performance data to a remote system or any other suitable computing device. For example, the device 1800 may attempt to forward collected performance data to a remote system immediately after collection, at a prescheduled interval, and/or upon the detection of a network connection to the remote system, or some combination thereof.

In other aspects of the present disclosure, performance data recorded by device 1800 may further be published or shared in one or more outlets. The user interface may provide the user with various tools or interface elements (e.g., icons) that permit the user to share recorded performance data and athletic activity metrics with other users and/or to post to a social networking website. The user may also input a message (e.g., "1-month Wear Test") to accompany the performance metrics and data being sent. The device 1800 (or other computing device) may distribute performance data of a current and/or previous monitoring session and the message to another computing device. For example, device 1800 may transmit to a server an electronic data file containing the performance data depicted in oscilloscope display 2010 as illustrated in FIG. 20A in response to a user initiating the "Send" icon 2012.

In some arrangements, the electronic data file may include a csv file and/or any may be comprise any other suitable type of file format to display the recorded performance data. In some embodiments, the electronic data file may include other information associated with the USB device (and/or corresponding sensor and sensor components) that recorded the performance data therein. For example, the data file may include the name of the USB device and corresponding sensor (or sensor components), the device configuration settings and specifications used to record the performance data during the monitoring session, device information displayed in the user interface, and any other device-related information recorded or collected by device 1800. The server may incorporate the performance data and/or message in the social networking website and/or may distribute the data/message to other desired or all users. As yet another example, performance data may be published as a news entry on a user's social network page. Alternatively, the performance data may be published as a status entry on a user's social messaging site. The user may further limit the types and/or amount of information publicly displayed. As yet another example, the performance data may be transmitted in an electronic-mail message (or other suitable type of message) to other users or groups of users.

Figure 22A:
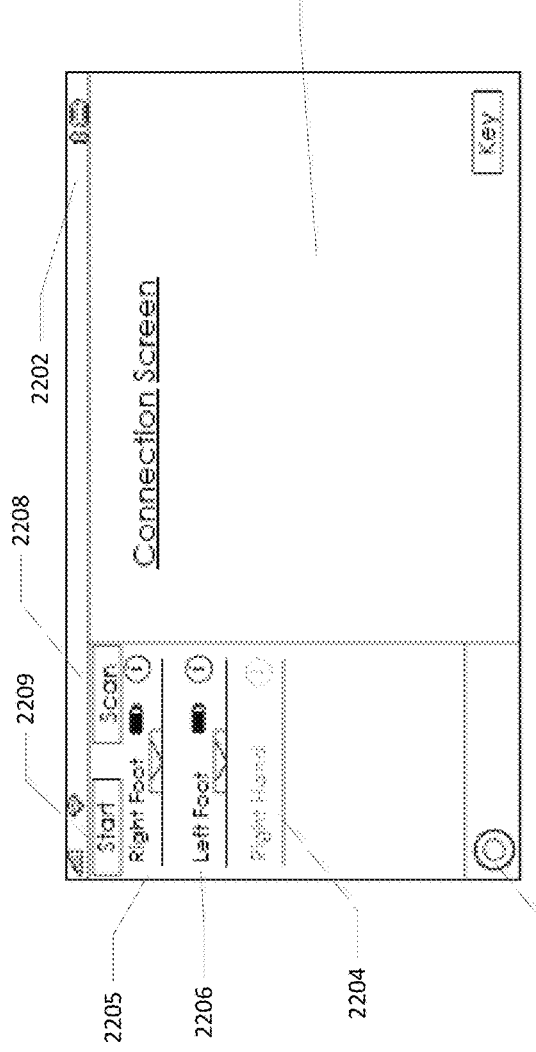

FIGS. 22A-F illustrate additional exemplary interface screens that may be displayed to the user in accordance with at least some embodiments of the present disclosure. As depicted in the example embodiment depicted in FIG. 22A, interface 2201 may include a first portion 2202 that lists or displays the various sensors and/or sensor components of the one or more USB devices detected by (or within a threshold proximity to) device 1800. In some embodiments, the interface display 2202 may distinguish sensors (or sensor components) that have established a communication relationship with device 1800 from those sensors that have not established a communication relationship. In some arrangements, the indicia representing a sensor that has not established a communication relationship with device 1800 may be partially or substantially obscured in order to visually emphasize other portions of the interface display 2202. For example, as illustrated in FIG. 22A, in some example embodiments, interface display 2204 is partially obscured (e.g., "greyed-out") such that interface portions 2205 and 2206 are visually emphasized to the user. Display screen 2210 of interface 2201 may be configured to display various types of information to the user. As illustrated in FIG. 22A, in other aspects of the present disclosure display screen 2210 may display performance data, and provide the same features and functionalities as the oscilloscope display interface (e.g., interface 2010) as described above with reference to FIG. 20A.

In some aspects of the present disclosure, as illustrated in the example embodiment depicted in FIG. 22A, a user may attempt locate one or more devices (e.g., USB devices, sensors, sensor components, etc.) capable of establishing a communication relationship with device 1800 by selecting or otherwise interacting with the "Scan" icon (e.g., icon 2208). Additionally, a user may initiate a performance monitoring session with one or more detected devices by selecting the "Start" icon (e.g., icon 2209). For example, by selecting Start icon 2209, the device 1800 may transmit a command signal to the "Right foot" and "Left foot" sensors to begin collecting performance data. In some aspects of the present disclosure, a user may access an interface providing instructions and/or assistance with operating the software application by selecting the "Help" icon 2207.

Figure 22B:
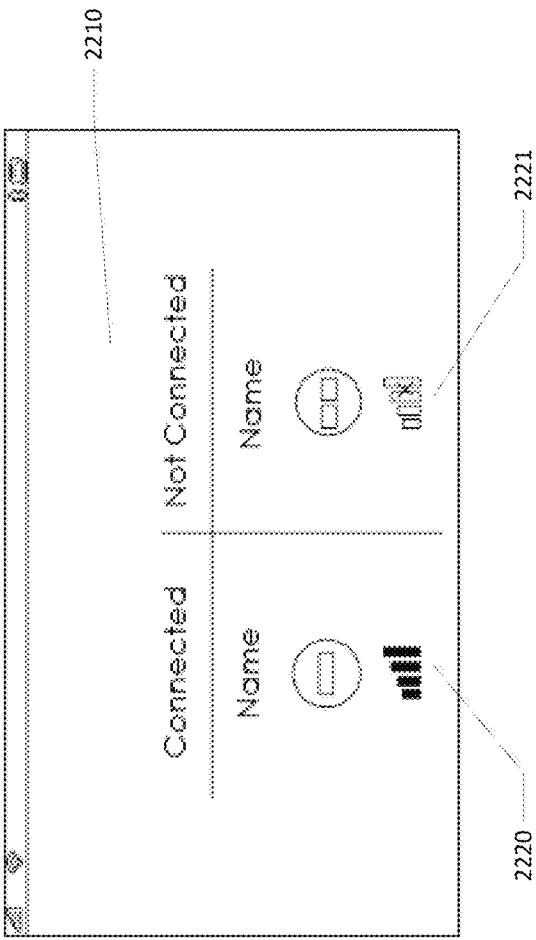

In other aspects of the present disclosure, as depicted by display screen 2010 in the example embodiment depicted in FIG. 22B, the interface display screen may display indicia 2220 (e.g., symbol, graphic, indicator, etc.) indicating a relative strength of a communication connection between the USB device, sensor or sensor component and device 1800. Additionally or alternatively, the interface display may display a particular graphic and/or other indicator (e.g., element 2221) in the display screen to indicate that a detected USB device is not connected to device 1800.

Figure 22C:
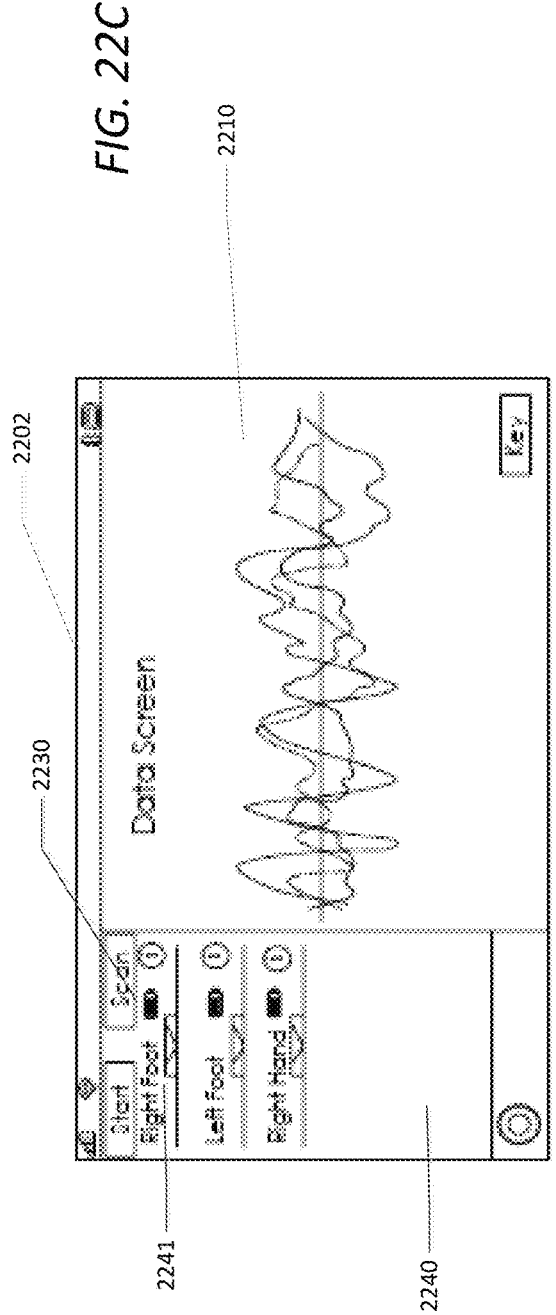
Figure 22D:
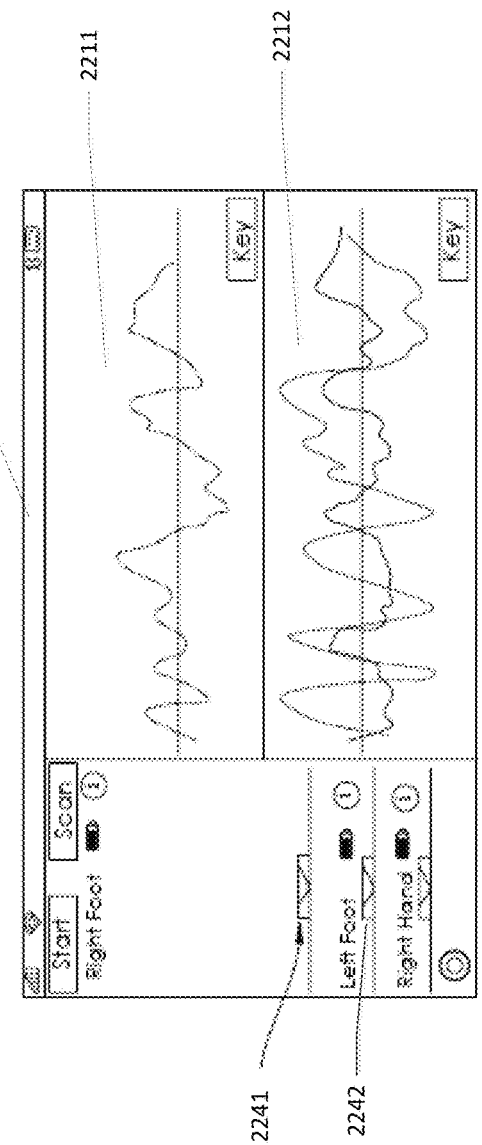

In some aspects of the present disclosure, as depicted by element 2230 in the example embodiment depicted in FIG. 22C, an interface display screen may display an indicia (e.g., symbol, graphic, indicator, etc.) indicating a level of power supply (or capacity) remaining in a detected USB device, sensor, and/or sensor component. Additionally, as illustrated in the example embodiment depicted in FIGS. 22C-D, a user may modify the shape, size, location, and other aspects of the various portions of interface 2202. In some aspects of the present disclosure, a user may be able to configure interface 2202 to view performance data obtained by individual USB devices, sensors, and/or sensor components in their own, separate interface display screen (e.g., sub-interface). A user may select, via an input system, a portion 2241 (e.g., icon 2241) of interface display 2240 to display the performance data associated with the "right foot" sensor in a separate sub-interface. For example, the user may tap, select, swipe or perform any other suitable interaction with icon 2241 to cause the interface display 2210 to show the performance data for the "right foot" sensor in a separate sub-interface. As shown in the example embodiment depicted in FIG. 22D, the performance data collected by the sensor labeled "right-foot" is displayed in a first sub-interface 2211, while the performance data collected by the remaining sensors (e.g., sensors labeled "left-foot" and "right hand") are displayed in a second sub-interface 2212. In some arrangements, by selecting icon 2241 a second time, the performance data associated with the "right-foot" sensor may be displayed in the same interface display as the performance data for the "left-foot" and "right-hand" sensors.

In some aspects of the present disclosure, as illustrated in the example embodiment depicted in FIG. 22E, if a user selects icon 2242, the interface 2202 may generate a third separate sub-interface displaying the performance data associated with the "left foot" sensor. For example, FIG. 22F illustrates interface 2202 after a user has selected icon 2242 as described above with respect to FIG. 22E. As depicted in FIG. 22F, interface 2202 has created a third separate sub-interface (i.e., sub-interface 2213) displaying the performance data for the "left foot" sensor. Additionally, the performance data for the right hand sensor is still displayed in the second sub-interface (i.e., sub-interface 2212). The interface 2202 may be configured to permit the user to view and/or modify the display of performance data associated for various devices, sensors, and/or sensor components during a performance monitoring session (e.g., while data is being streamed in real-time from a sensor to device 1800). In other aspects of the present disclosure, the interface 2202 may provide the user with a display menu allowing the user to configure the display interface and choose which of the various sensors and their corresponding performance data should be displayed in the same (or separate) sub-interface.

In some aspects of the present disclosure, additional registration features can be provided with the software application wherein additional features can be provided to the user for use with the USB device 16. The software can additionally have a guest log in, which allows the user to upload data automatically from the USB device without requiring the user to register. This feature allows the user to use the software without giving personal information. Later, if the user decides to register the USB device, a unique PIN number associated with each USB device is matched up with registration information automatically.

Additionally or alternatively, the user interface described herein may also be configured to allow a user to selectively activate and de-activate features according to the preferences of the user. The user may also be able to modify software associated with the USB device. For example, one or more algorithms, which may be stored as computer-executable instructions on a tangible computer-readable medium within the housing of the USB device, may be implemented to control the measurement of performance data for one or more sensors and/or the calculation of performance metrics. In some aspects of the present disclosure, the one or more algorithms may determine and/or control the sampling rate of a detected USB device, sensor, sensor component, etc. In some embodiments where a programmed algorithm is used to control the measurement of performance data and metrics, the user may not have the option to access a device configuration interface for configuring the USB device, sensors, and/or sensor components as described herein. In such arrangements, the software application may be configured to adjust the various parameters and settings for the USB device, sensors, and/or sensor components in accordance with predetermined parameters established by the algorithm.

Device Operational Modes:

In some aspects of the present disclosure, the USB device may be selectively and/or automatically operated in a plurality of different operational modes, wherein certain operational aspects or features of the USB device are available for each of the various operational modes. In some embodiments, when the USB device may be operated in a "PowerOff" mode when the USB device is powered off. In the PowerOff mode, all of the sensors and other electronic components of the USB device may be powered off. In some arrangements, during the PowerOff mode, the controller 21 may be operated in a lower power state, and may be further configured to wait for further signal input, such as a button press, signal input from a computing device, and the like. In such arrangements, the controller 21 may be configured to cause the USB device to begin operating in a second operational mode. For example, as described above with respect to FIGS. 9A-B, upon detecting a press of push button 33, the controller 21 may be configured to cause the USB device to power on (e.g., to operate in a PowerOn mode). When it is determined that the USB device is in the PowerOn mode, the one or more sensors and/or sensor components of the USB device may be enabled. In some embodiments, although a sensor may be enabled during the PowerOn mode, the sensor may not become active (e.g., begin collecting performance data). In other embodiments, when it is determined that the USB device is in the PowerOn mode, the transmission system (e.g., Bluetooth circuitry and/or components) may be activated and may begin broadcasting signals to other computing devices. Additionally, when it is determined that the USB device is in the PowerOn mode, controller 21 may be operated in an active state, and may be further configured to wait for further signal input, such as a button press, signal input from a computing device (e.g., device 1800) and the like. For example, in some arrangements, a user may initiate a performance monitoring session via a software application executing on device 1800. In this example, upon initiation of the performance monitoring session, the device 1800 may transmit a signal (indicating the start of the session) to the controller 21 of the USB device.

In other aspects of the present disclosure, the USB device may be operated selectively and/or automatically in a "Sleep" mode. In some embodiments, the USB device (or controller 21) may determine whether any new data is being accumulated by a sensor within or operatively connected to the USB device. Such a determination may, for example, involve an assessment of whether the sensor has ceased generating a signal or data for more than a particular period of time, e.g., several seconds. When it is determined that the sensor has ceased accumulating data, the USB device may transition from an active mode (e.g., PowerOn mode) to a Sleep mode for power preservation purposes. When it is determined that the USB device is in the Sleep mode, the transmission system (e.g., Bluetooth circuitry and/or components) may be disabled and/or may no longer advertise (e.g., broadcast signals to other devices). In some embodiments, when it is determined that the USB device is in the Sleep mode, one or more of the sensors within and/or operatively connected to the USB device may be disabled. In other arrangements, all of the sensors within and/or operatively connected to the USB device may be disabled, except for an accelerometer (or other sensor) that may utilized to detect motion for a "wake-up" function, which will be described in more detail below.

In some aspects of the present disclosure, when it is determined that the USB device is in the Sleep mode, data stored in one or more memory units (e.g., data stored in RAM) may be retained. Additionally, when it is determined that the USB device is in the Sleep mode, controller 21 may be configured to cause a time clock (e.g., real time clock) for the USB device to continue running. In other aspects of the present disclosure, when it is determined that the USB device is in the Sleep mode, the controller 21 may be operated in a sleep state, and may be further configured to wait for further signal input, such as a button press. In other arrangements, the controller 21 may continue to operate in the sleep state, until a determination is made that the USB device should "wake up" to begin actively processing and accumulating performance data once again. The determination of whether and when to wake up may be made, for example, by monitoring an output of a sensor (e.g., an accelerometer, a transducer, etc.) for activity, in a response to a user input, e.g., depression of a button 33, or by any other mechanism. For example, the controller may be configured to perform a "wake-up" function after detecting continuous accelerometer (or other sensor) activity for a predetermined time period, e.g., 15 seconds. In such arrangements, upon performing the "wake-up" function, the USB device may be operated in a PowerOn mode, or alternatively as will be explained in more detail below, a "Session" mode.

In some embodiments in which a sensor is used to monitor locomotion of a person on foot, the "wake up" determination may be made, for example, by employing a low-power comparator to monitor the output of a transducer. In embodiments in which an accelerometer that does not consume power is employed as the transducer, the power consumption of the USB device in the "Sleep" mode may thus be substantially limited to only the power consumption of such a comparator. It should be appreciated that in addition to such an automated "wake up" function, the USB device may additionally or alternatively include one or more user input devices, e.g., switches or pushbuttons (e.g., button 33), that may be manipulated to cause the USB device to "wake up." Furthermore, one or more user input devices may additionally or alternatively be provided that can be manipulated to cause the USB device to be put into a "sleep" mode, or even to cause the device to be powered down completely so that even the automated "wake up" function is disabled until further user input is provided.

In some aspects of the present disclosure, the USB device may be operated selectively and/or automatically in a "Session" mode. In some embodiments, the USB device may begin operating in the Session mode in response to receiving user input, e.g., depression of a button 33. In other embodiments, the USB device may begin operating in the Session mode in response to receiving an input put signal from a device (e.g., device 1800), or by any other suitable mechanism. In some aspects of the present disclosure, when it is determined that the USB device is in the Session mode, one or more sensors and/or sensor components of the USB device may be activated and may begin to collect/record performance data.

In some arrangements, as described above with respect to FIG. 19B, a user may utilize a user interface to determine or modify which sensors and/or sensor components of the USB device are activated during a performance monitoring session. In other embodiments, when it is determined that the USB device is in the Session mode, the transmission system (e.g., Bluetooth circuitry and/or components) of the USB device may be activated such that performance data collected by one or more sensors is transmitted to a device (e.g., device 1800) that has established a communication relationship with the USB device. In other arrangements, the transmission system may be disabled during the Session mode if performance data collected by the one or more sensors is not being transmitted to another computing device. In still other embodiments, when it is determined that the USB device is in the Session mode, the controller 21 may be operated in an active state, and may be further configured to wait for further signal input, such as a button press and/or signal input from a computing device (e.g., device 1800). For example, in some arrangements, a user may end a performance monitoring session via a software application executing on device 1800. In this example, upon ending the performance monitoring session, the device 1800 may transmit a signal (indicating the session has ended) to the controller 21 of the USB device.

As described above, in some aspects of the present disclosure, the USB device may be operated selectively and/or automatically in a first operational mode in which one or more sensors (and/or sensor components), the controller 21, and the transmission system are used at least occasionally to obtain and transmit performance data to a second device (e.g., device 1800). When it is determined that the battery 38 is in a low power condition, the USB device may be operated in a second operational mode wherein the one or more sensors (and/or sensor components), controller 21, and transmission system are not used to obtain and transmit processed performance data to the second device, but wherein the USB device at least occasionally transmits a signal to the second device that indicates a low power condition of the battery.

As described above, in some embodiments, upon detecting a "low power" condition of a power supply (e.g., battery 38), the mode of operation of the USB device may be changed so as to substantially reduce its rate of power consumption. The USB device may then be allowed to perform only a limited set of functions, and in some arrangements, may transmit a "low power" signal to a computing device (e.g., device 1800) for an extended period of time in spite of its decreased functionality. In certain embodiments, the USB device may be configured so that the only function it performs while in its "low power" mode of operation is the transmission of a signal to the computing device informing the computing device of its "low power" condition. In some embodiments, as described above, the capacity or usage of the battery may additionally be monitored, and the USB device (and/or device 1800) may determine when the battery (e.g., battery 38) is soon to be in a "low power" condition and a signal is transmitted indicating such to be the case, thus enabling the user to be warned that the battery is "running low and needs to be replaced soon," or to be provided with some similar message or indication.

Should the user fail to replace the battery before the "low power" condition is actually reached, the device will not simply cease working, but will change modes of operation so as to substantially reduce its power consumption and will continue to inform the user of the "lower power" condition of the battery. Accordingly, unlike with prior art remote sensor devices that cease all operations after they run out of power, a user of a device like that disclosed herein will not be left guessing as to whether the system including the remote device ceased working because the remote device ran out of power or because of some other reason, such as failure of one or more other components of the remote device or failure of one or more components of the receiving device.

For the avoidance of doubt, the present application extends to the subject-matter described in the following numbered paragraphs (referred to as "Para" or "Paras"):

1. A wearable device assembly comprising:
    a wearable device comprising:
    a housing having a first end and a second end;
    a first connector attached to the first end of the housing and configured to transmit to and receive data from an external computing device;
    a user input system;
    a controller supported by the housing; and
    a processor configured to obtain performance data using a sensor operably associated with the controller; and
    a first ancillary member having a second connector configured to mate with the first connector of the wearable device so as to detachably connect the first ancillary member to the device.

2. A wearable device assembly according to Para 1, wherein the controller has a first sensor operably associated therewith, wherein the first sensor is configured to detect a first parameter of an athletic performance of a user.

3. A wearable device assembly according to Para 1 or 2, wherein the first ancillary member includes at least a second sensor configured to be operably associated with the controller when the first connector is connected to the second connector such that the second sensor is configured to detect a second parameter of the athletic performance of the user.

4. A wearable device assembly according to Para 3, wherein the first ancillary member includes at least a first indicia indicating a sensor type of the second sensor.

5. A wearable device assembly according to any of the preceding Paras, wherein the first ancillary member includes a rechargeable power source configured to provide a power supply to at least one of the first ancillary member and the device.

6. A wearable device assembly any of the preceding Paras, wherein the housing further comprises an internal battery, the first connector being further configured to transmit power received from an external power source to the internal battery.

7. A wearable device assembly according to any of the preceding Paras, wherein the first and second connectors are USB connectors.

8. A wearable device assembly according to any of the preceding Paras, wherein the first connector is a male plug and the second connector is a female receptacle which is configured to receive the male plug.

9. A wearable device assembly according to any of the preceding Paras, further comprising: an indicator system comprising one or more lighting elements.

10. A wearable device assembly according to any of the preceding Paras, wherein the first ancillary member has a first end and a second end, wherein the connector is attached to the first end.

11. A wearable device assembly according to any of the preceding Paras, further comprising a memory storing computer readable instructions that, when executed by the wearable device, cause the processor to at least:
   receive a user input through the user input system configured to initiate a performance monitoring session; and
   in response to the received user input, transmit to a computing device, performance data obtained by the sensor.

12. A wearable device assembly according to Para 11, wherein the memory further comprises computer readable instructions that, when executed, further cause the processor to at least:
   determine a type of user input received through the user input system, wherein the type of user input corresponds to a type of interaction with the user input system.

13. A wearable device assembly according to Para 12, wherein the type of user input is determined based at least in part on a duration of the user input.

14. A wearable device assembly according to any of the preceding Paras, further comprising a transceiver, wherein the memory further comprises computer readable instructions that, when executed, further cause the processor at least to:
   transmit via the transceiver, to a wrist-worn computing device, a first set of performance metrics.

15. A wearable device assembly according to any of the preceding Paras, wherein the user input system comprises at least a first push button adapted to be associated with the controller, and wherein the first push button is integral with the housing.

16. An athletic performance monitoring system, comprising:
   a portable electronic device including a first connector configured to transmit and receive data from an external computing device;
   a first ancillary member comprising a second connector configured to mate with the first connector;
   wherein the portable electronic device includes a first sensor configured to detect a first type of athletic activity data relating to an athletic performance of a user and/or the first ancillary member includes at least a second sensor configured to detect a second type of athletic activity data relating to the athletic performance of the user; and
   a display device configured to display information associated with the athletic performance during the athletic performance using the first type and/or second type of athletic activity data.

17. An athletic performance monitoring system according to Para 16, wherein the first and second connectors are USB connectors.

18. An athletic performance monitoring system according to Para 16 or 17, wherein the first connector is a male plug and the second connector is a female receptacle which is configured to receive the male plug.

19. An athletic performance monitoring system according to any of Paras 16 to 18, further comprising:
   a second ancillary member comprising a third connector configured to mate with the first connector, wherein the second ancillary member includes a third sensor configured to detect a third type of athletic activity data relating to the athletic performance of the user.

20. An athletic performance monitoring system according to any of Paras 16 to 18, further comprising:
   a second ancillary member comprising a third connector configured to mate with the first connector, wherein the second ancillary member includes a rechargeable power source configured to provide a power supply to at least one of the first ancillary member and the portable electronic device.

21. An athletic performance monitoring system according to any of Paras 16 to 20, further comprising:
   a piece of athletic equipment including a securing element, such as an aperture, configured to removably receive the first connector.

22. An athletic performance monitoring system according to any of Paras 16 to 21, further comprising:
   a data transmission system engaged with the portable electronic device, wherein the data transmission system is configured to transmit data from the portable electronic device for receipt by the display device, wherein the data transmitted includes at least the first type of athletic activity data.

23. A method comprising:
   receiving, by a portable electronic device, a first set of athletic performance data including a first activity metric associated with an athletic performance of a user;
   determining that a first ancillary member is physically engaged with the portable electronic device to produce a first device assembly configured to provide a second set of athletic performance data including a second activity metric associated with the athletic performance of the user.

24. A method according to Para 23, further comprising:
   determining the first ancillary member is physically engaged with the portable electronic device in a first orientation; and
   in response to determining the first ancillary member is physically engaged with the portable electronic device in the first orientation, activating, by an activation system, a first function of the portable electronic device that is not available when the first ancillary member is not physically engaged with the portable electronic device.

25. A method according to Para 24, further comprising:
   deactivating at least the first function of the portable electronic device when the portable electronic device is determined to be engaged with the first ancillary member in an orientation other than the first orientation.

26. A method according to any of Paras 23 to 25, wherein the first device assembly further comprises a connector, the method further comprising:
  determining that the connector of the assembly is engaged with a securing element of a piece of athletic equipment; and
  in response, determining at least one of: a location in or on the piece of athletic equipment and a type of the piece of athletic equipment with which the first device assembly has been engaged.

27. A method according to Para 25, further comprising:
  selecting a data processing algorithm from a plurality of algorithms based on, at least in part, the determined location in or on the piece of athletic equipment with which the device assembly has been engaged.

28. A method according to Para 26 or 27, further comprising:
  selecting a data processing algorithm from a plurality of algorithms based on, at least in part, the determined type of the piece of athletic equipment with which the device assembly has been engaged.

Conclusion

While the present disclosure has been described with respect to specific examples including presently preferred modes of carrying out the various embodiments of present disclosure, those skilled in the art will appreciate that there are numerous variations and permutations of the above described systems and methods. For example, various aspects of the present disclosure may be used in different combinations and various different subcombinations of aspects of the present disclosure may be used together in a single system or method without departing from the present disclosure. Also, various elements, components, and/or steps described above may be changed, changed in order, omitted, and/or additional elements, components, and/or steps may be added without departing from the scope of present disclosure. Thus, the present disclosure should be construed broadly as set forth in the appended claims.

We claim:

1. A wearable device assembly comprising:
  a housing containing an internal battery, and further having a first end and a second end;
  a USB connector attached to the first end of the housing, wherein the USB connector transmits to, and receives data from, an external computing device, and wherein the USB connector transmits power, received from an external power source, to the internal battery;
  a user input system;
  a controller supported by the housing, the controller having a first sensor operably associated therewith wherein the first sensor detects a first parameter of an athletic performance of a user;
  a first receiver member defining an opening to removably receive the USB connector, wherein the first receiver member includes at least a second sensor configured to be operably associated with the controller when the USB connector is received within the opening of the first receiver member, and wherein the second sensor detects a second parameter of the athletic performance of the user;
  a processor; and
  a memory storing computer readable instructions that, when executed by the processor, cause the wearable device assembly to at least:
    receive a user input through the user input system, wherein the received user input initiates a performance monitoring session; and
    in response to receiving the user input, transmit, to a computing device, performance data obtained by at least one of the first sensor and the second sensor.

2. The wearable device assembly of claim 1, further comprising:
  an indicator system comprising one or more lighting elements.

3. The wearable device assembly of claim 1, wherein the first receiver member includes a rechargeable power source that provides a power supply to at least the first sensor.

4. The wearable device assembly of claim 1, wherein the first receiver member has a first and a second end, wherein the first receiver member includes a USB connector attached to the first end.

5. The wearable device assembly of claim 1, wherein the memory further comprises computer readable instructions that, when executed, further cause the wearable device assembly to at least:
  determine a type of user input received through the user input system, wherein the type of user input corresponds to a type of interaction with the user input system.

6. The wearable device assembly of claim 5, wherein the type of user input is determined based at least in part on a duration of the user input.

7. The wearable device assembly of claim 5, further comprising a transceiver, wherein the memory further comprises computer readable instructions that, when executed, further cause the wearable device assembly at least:
  transmit, via the transceiver, to a wrist-worn computing device, a first set of performance metrics.

8. The wearable device assembly of claim 1, wherein the first receiver member includes at least a first indicia indicating a sensor type of the second sensor.

9. The wearable device assembly of claim 1, wherein the user input system comprises at least a first push button adapted to be associated with the controller, and wherein the first push button is integral with the housing.

10. A method comprising:
  receiving, by a portable USB device, a first set of athletic performance data including a first activity metric associated with an athletic performance of a user;
  determining, by a processor, that a first receiver member is physically engaged with the portable USB device in a first orientation to produce a first device assembly, wherein the first device assembly provides a second set of athletic performance data including a second activity metric associated with the athletic performance of the user; and
  in response to determining the first receiver member is physically engaged with the portable USB device in the first orientation, activating, by an activation system, a first function of the portable USB device that is not available when the first receiver member is not physically engaged with the portable USB device.

11. The method of claim 10, further comprising:
  deactivating at least the first function of the portable USB device when the portable USB device is determined to be engaged with the first receiver member in an orientation other than the first orientation.

12. The method of claim 10, wherein the first device assembly further comprises a first USB connector, the method further comprising:
  determining that the first USB connector is engaged with a securing element of a piece of athletic equipment; and
  in response to the determining that the first USB connector is engaged with the securing element of the piece of athletic equipment, determining at least one of: (i) a location on the piece of athletic equipment with which the first device assembly has been engaged, and (ii) a type of the piece of athletic equipment with which the first device assembly has been engaged.

13. The method of claim 12, further comprising:
selecting a data processing algorithm from a plurality of algorithms based on the determined location on the piece of athletic equipment with which the first device assembly has been engaged.

14. The method of claim 12, further comprising:
selecting a data processing algorithm from a plurality of algorithms based on the determined type of the piece of athletic equipment with which the first device assembly has been engaged.

15. A portable computing device:
a processor; and
a memory storing computer readable instructions that, when executed by the processor, cause the portable computing device to at least:
receive a first set of athletic performance data including a first activity metric associated with an athletic performance of a user;
determine that a first receiver member is physically engaged with the portable computing device in a first orientation to produce a first device assembly, wherein the first device assembly provides a second set of athletic performance data including a second activity metric associated with the athletic performance of the user; and
in response to determining the first receiver member is physically engaged with the portable computing device in the first orientation, activate, by an activation system, a first function of the portable computing device that is not available when the first receiver member is not physically engaged with the portable computing device.

16. The portable computing device of claim 15, wherein the memory further comprises computer readable instructions that, when executed, further cause the portable computing device to at least:
determine that the portable computing device is engaged with the first receiver member in an orientation other than the first orientation; and
in response to determining that the portable computing device is engaged with the first receiver member in the orientation other than the first orientation, deactivate at least the first function of the portable computing device.

17. The portable computing device of claim 15, wherein the portable computing device further comprises a first USB connector, and wherein the memory further comprises computer readable instructions that, when executed, further cause the portable computing device to at least:
determine that the first USB connector is engaged with a securing element of a piece of athletic equipment; and
in response to the determining that the first USB connector is engaged with the securing element of the piece of athletic equipment, determining at least one of: (i) a location on the piece of athletic equipment with which the first device assembly has been engaged, and (ii) a type of the piece of athletic equipment with which the first device assembly has been engaged.

18. The portable computing device of claim 17, wherein the memory further comprises computer readable instructions that, when executed, further cause the portable computing device to at least:
select a data processing algorithm from a plurality of algorithms based on the determined location on the piece of athletic equipment with which the first device assembly has been engaged.

19. The portable computing device of claim 17, wherein the memory further comprises computer readable instructions that, when executed, further cause the portable computing device to at least:
select a data processing algorithm from a plurality of algorithms based on the determined type of the piece of athletic equipment with which the first device assembly has been engaged.

* * * * *

UNITED STATES PATENT AND TRADEMARK OFFICE
CERTIFICATE OF CORRECTION

PATENT NO. : 9,724,562 B2
APPLICATION NO. : 14/723901
DATED : August 8, 2017
INVENTOR(S) : Bailly et al.

It is certified that error appears in the above-identified patent and that said Letters Patent is hereby corrected as shown below:

In the Claims

Column 52, Claim 7 Line 29:
After "assembly", insert --to--

Column 52, Claim 7 Line 30:
Delete "transceiver," and insert --transceiver-- therefor Signed and Sealed this
Eighteenth Day of April, 2023

Katherine Kelly Vidal
*Director of the United States Patent and Trademark Office*